US011452770B2

(12) United States Patent
Kim et al.

(10) Patent No.: US 11,452,770 B2
(45) Date of Patent: Sep. 27, 2022

(54) RECOMBINANT VACCINIA VIRUS AND USE THEREOF

(71) Applicant: KOLON LIFE SCIENCE, INC., Seoul (KR)

(72) Inventors: Sujeong Kim, Seoul (KR); Minjung Kim, Seoul (KR); Heonsik Choi, Seoul (KR); Jaeil Shin, Seoul (KR); Minju Kim, Seoul (KR); Hyesun Lee, Seoul (KR); Soondong Lee, Gwangmyeong-si (KR); Hwanjun Choi, Incheon (KR); Joonsung Kim, Gimpo-si (KR); Jieun Hong, Seoul (KR); Eunjin Lee, Seoul (KR)

(73) Assignee: KOLON LIFE SCIENCE, INC., Seoul (KR)

( * ) Notice: Subject to any disclaimer, the term of this patent is extended or adjusted under 35 U.S.C. 154(b) by 0 days.

(21) Appl. No.: 16/319,067

(22) PCT Filed: Jul. 21, 2017

(86) PCT No.: PCT/KR2017/007896
§ 371 (c)(1),
(2) Date: Jan. 18, 2019

(87) PCT Pub. No.: WO2018/016917
PCT Pub. Date: Jan. 25, 2018

(65) Prior Publication Data
US 2019/0247487 A1    Aug. 15, 2019

(30) Foreign Application Priority Data
Jul. 21, 2016 (KR) .................. 10-2016-0092684

(51) Int. Cl.
*A61K 39/275* (2006.01)
*A61K 39/12* (2006.01)
(Continued)

(52) U.S. Cl.
CPC ............ *A61K 39/12* (2013.01); *A61K 35/768* (2013.01); *A61K 39/0011* (2013.01);
(Continued)

(58) Field of Classification Search
None
See application file for complete search history.

(56) References Cited

U.S. PATENT DOCUMENTS

| 5,766,599 A | 6/1998 | Paoletti et al. |
| 8,506,947 B2 * | 8/2013 | McCart ................. C12N 15/86 424/93.1 |

(Continued)

FOREIGN PATENT DOCUMENTS

| EP | 1 955 703 A1 | 8/2008 |
| JP | 6-505874 A | 7/1994 |

(Continued)

OTHER PUBLICATIONS

Qin et al., "Evolution of and Evolutionary Relationships between Extant Vaccinia Virus Strains," Journal of Virology, vol. 89, No. 3: 1809-1824 (Year: 2015).*

(Continued)

*Primary Examiner* — M Franco G Salvoza
(74) *Attorney, Agent, or Firm* — Sughrue Mion, PLLC

(57) ABSTRACT

The present invention relates to a recombinant vaccinia virus in which the expression of some genes is inhibited, and a use thereof. The recombinant vaccinia virus of the present invention selectively kills cancer cells, and has an excellent reproducibility in cancer cells. Also, the virus has a lower toxicity to normal cells, and thus has an advantage of being safe for a human body. Therefore, the recombinant vaccinia virus of the present invention can be effectively used as a composition for treating cancer.

11 Claims, 9 Drawing Sheets
Specification includes a Sequence Listing.

(51) Int. Cl.
*C12N 7/00* (2006.01)
*A61K 35/768* (2015.01)
*A61P 35/00* (2006.01)
*A61K 39/00* (2006.01)

(52) U.S. Cl.
CPC ............... *A61P 35/00* (2018.01); *C12N 7/00* (2013.01); *A61K 2039/525* (2013.01); *A61K 2039/585* (2013.01); *C12N 2710/24121* (2013.01); *C12N 2710/24134* (2013.01)

(56) References Cited

U.S. PATENT DOCUMENTS

| | | | |
|---|---|---|---|
| 9,492,534 | B2 | 11/2016 | Szalay et al. |
| 9,765,305 | B2 | 9/2017 | Qin et al. |
| 2012/0308484 | A1* | 12/2012 | Szalay ............... A61P 15/00 424/9.3 |

FOREIGN PATENT DOCUMENTS

| | | |
|---|---|---|
| JP | 2007-20586 A | 2/2007 |
| JP | 2016-520298 A | 7/2016 |
| KR | 10-2014-0032991 A | 3/2014 |
| KR | 10-2016-0041831 A | 4/2016 |
| KR | 10-2016-0045227 A | 4/2016 |
| WO | 92/15672 A1 | 9/1992 |
| WO | 00/73479 A1 | 12/2000 |
| WO | WO-2005007824 A2 * | 1/2005 ............. C12N 15/86 |
| WO | 2013/163724 A1 | 11/2013 |
| WO | 2017/037523 A1 | 3/2017 |

OTHER PUBLICATIONS

Buijs et al., "Oncolytic viruses: From bench to bedside with a focus on safety," Human Vaccines & Immunotherapeutics, 11:7: 1573-1584 (Year: 2015).*

Patel et al., "Next generation approaches for tumor vaccination," Chinese Clinical Oncology, 6(2): 19 (Year: 2017).*

Amanda Rice, et al., "Roles of Vaccinia Virus Genes E3L and K3L and Host Genes PKR and RNase L during Intratracheal Infection of C57BL/6 Mice", Journal of Virology, Oct. 13, 2010, pp. 550-567, vol. 85, No. 1.

International Search Report for PCT/KR2017/007896 dated Jan. 2011 [PCT/ISA/210].

Naif Khalaf Alharbi et al., "Deletion of Fifteen Open Reading Frames from Modified Vaccinia Virus Ankara Fails to Improve Immunogenicity", Plos One, Jun. 8, 2015, vol. 10, No. 6, pp. 1-16 (16 pages total).

* cited by examiner

[Fig.1]
[Fig.2]
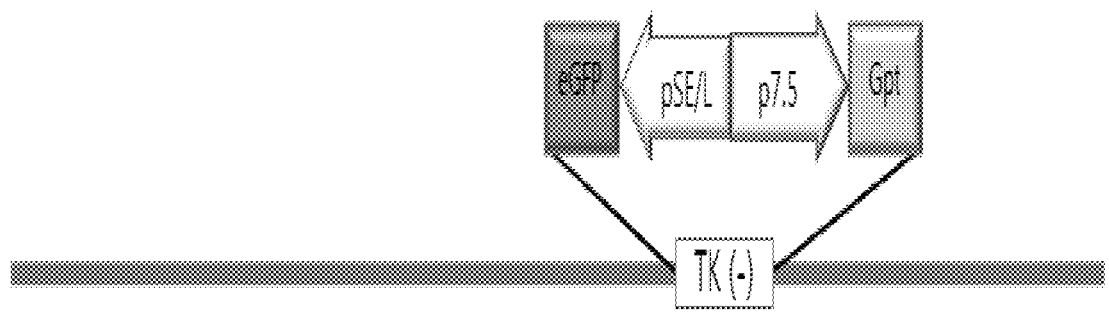
[Fig.3]
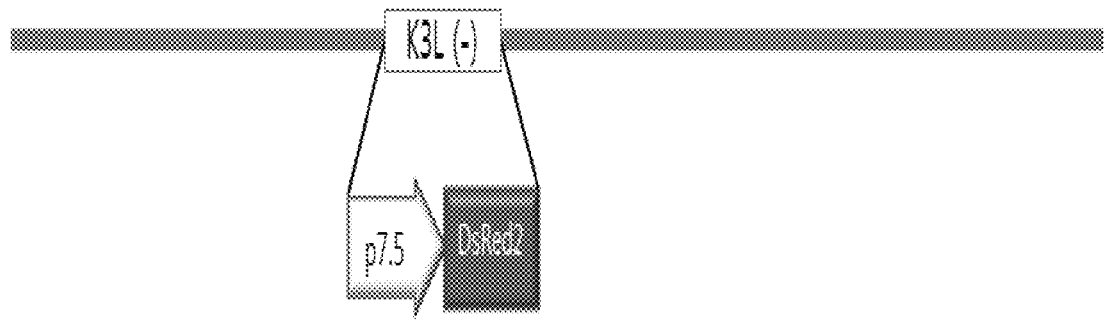

[Fig. 4A]
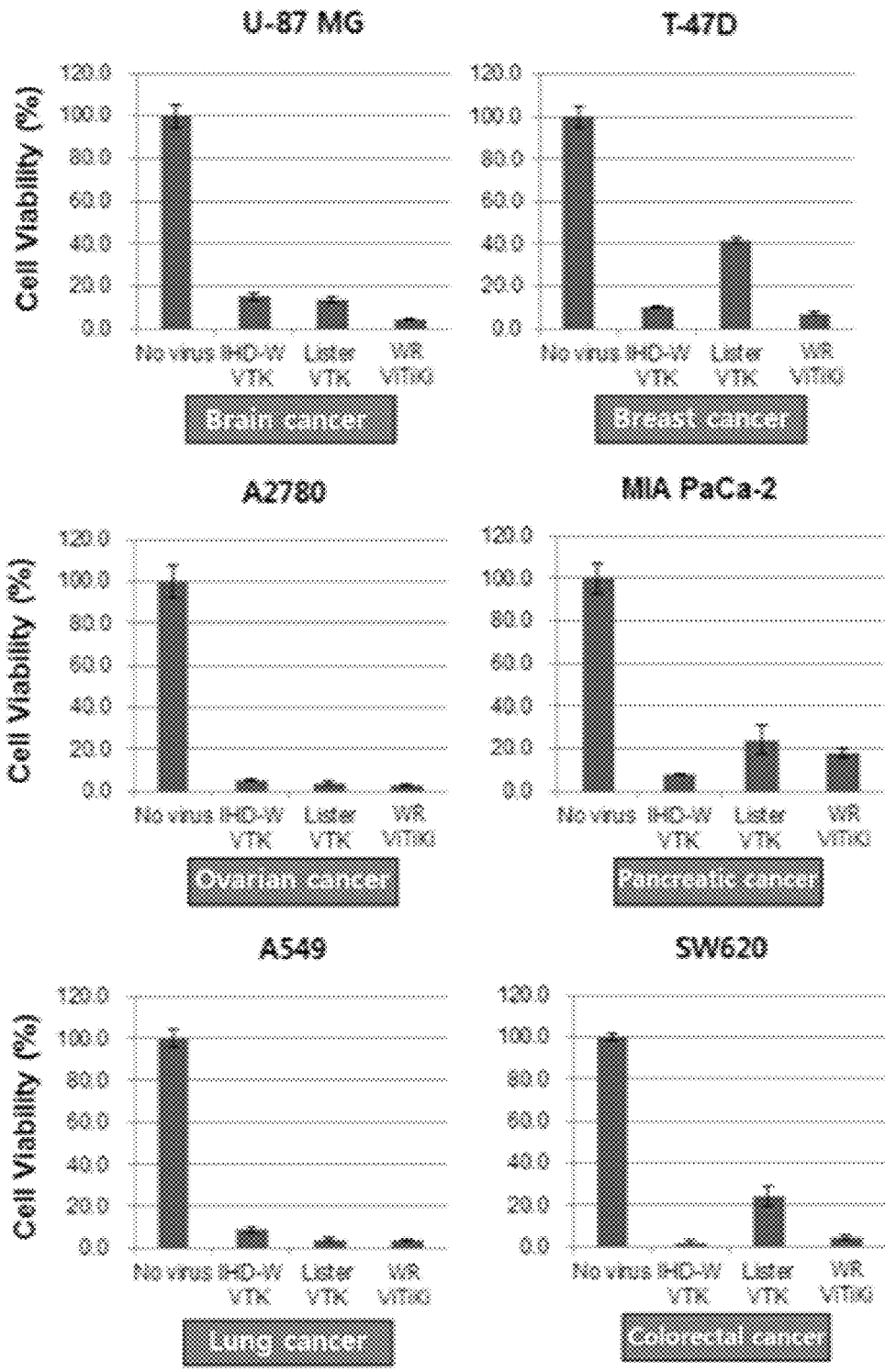

[Fig. 4B]
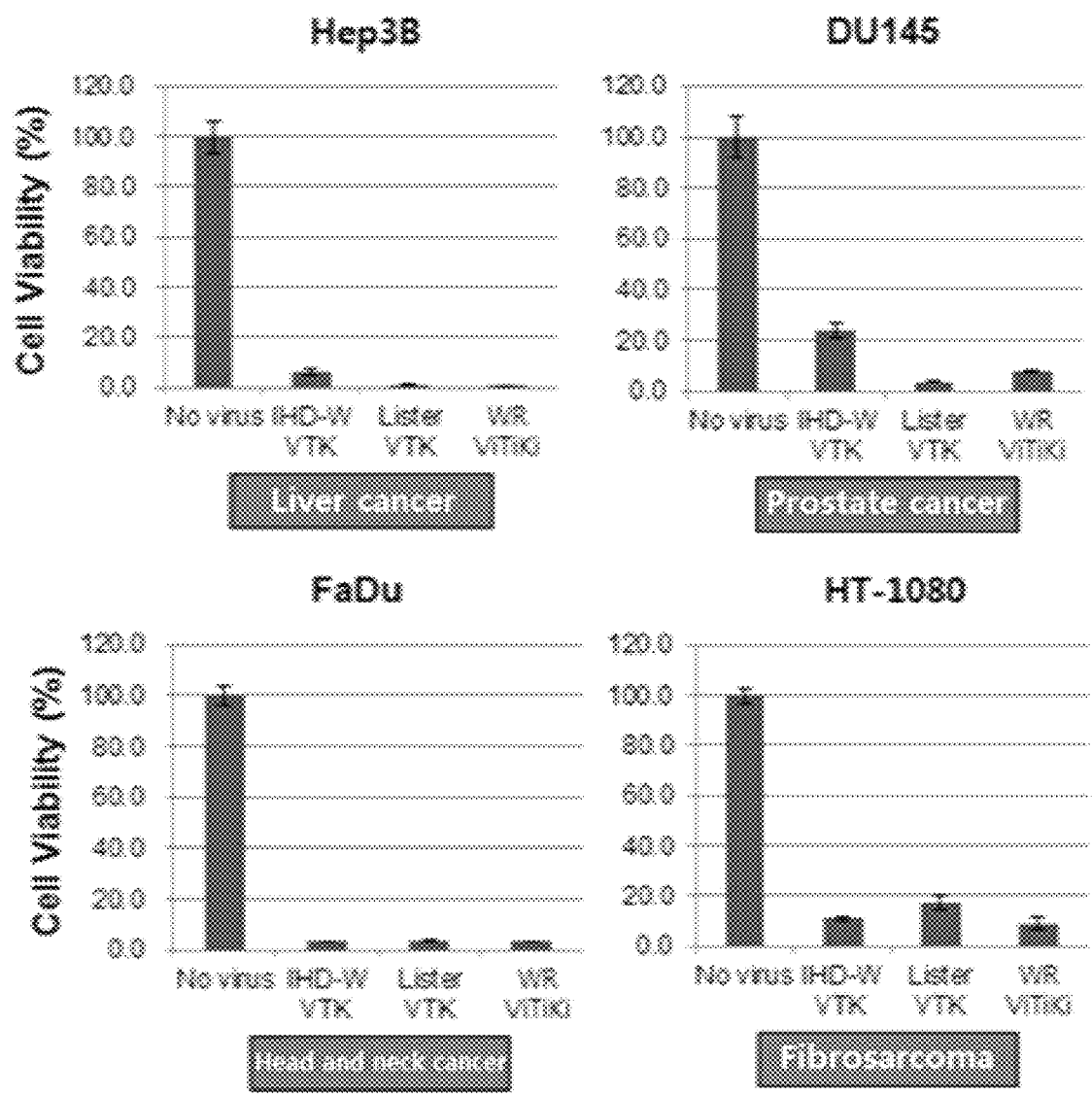

[Fig. 5]
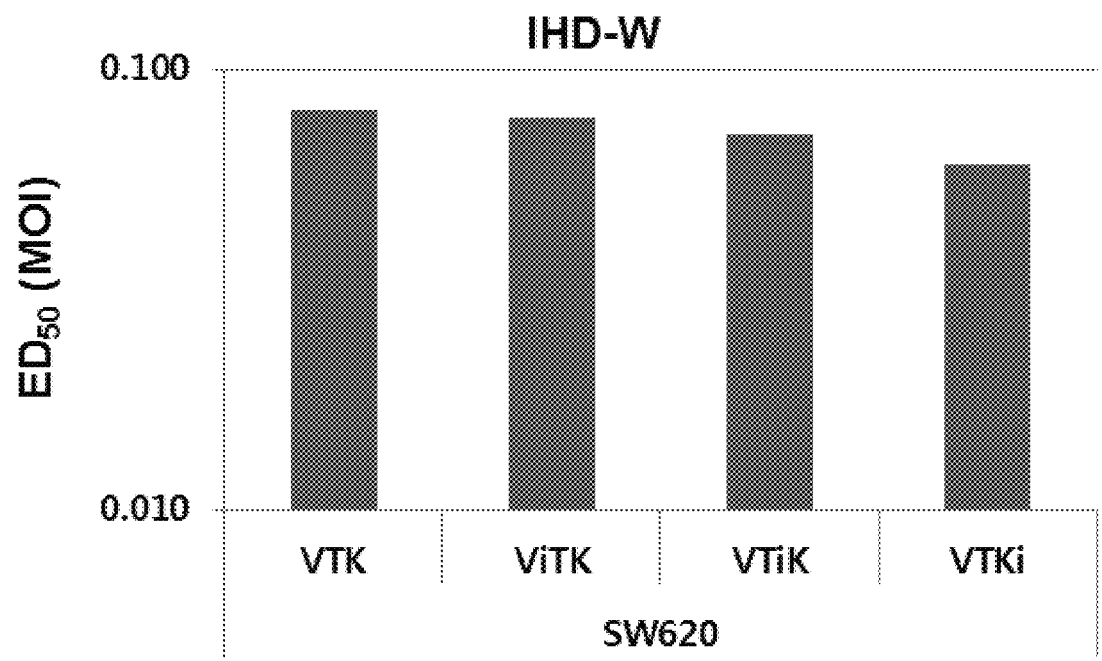

[Fig. 6A]
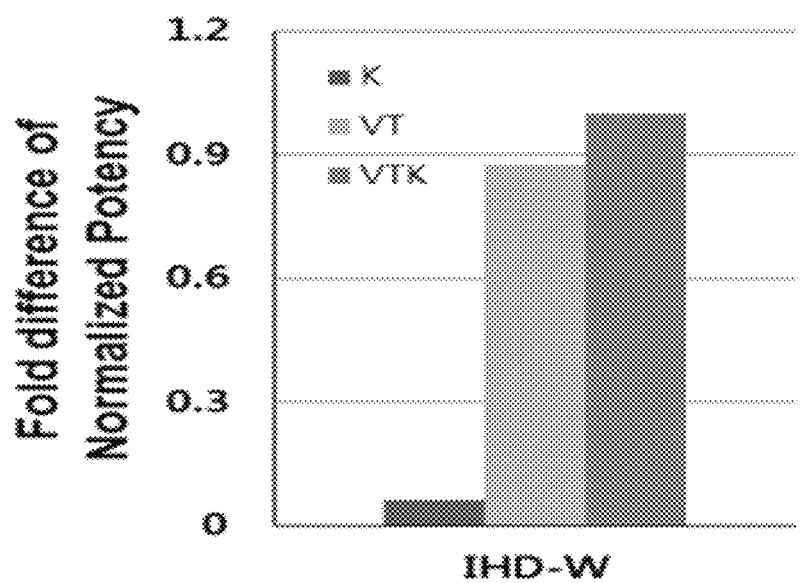
[Fig. 6B]
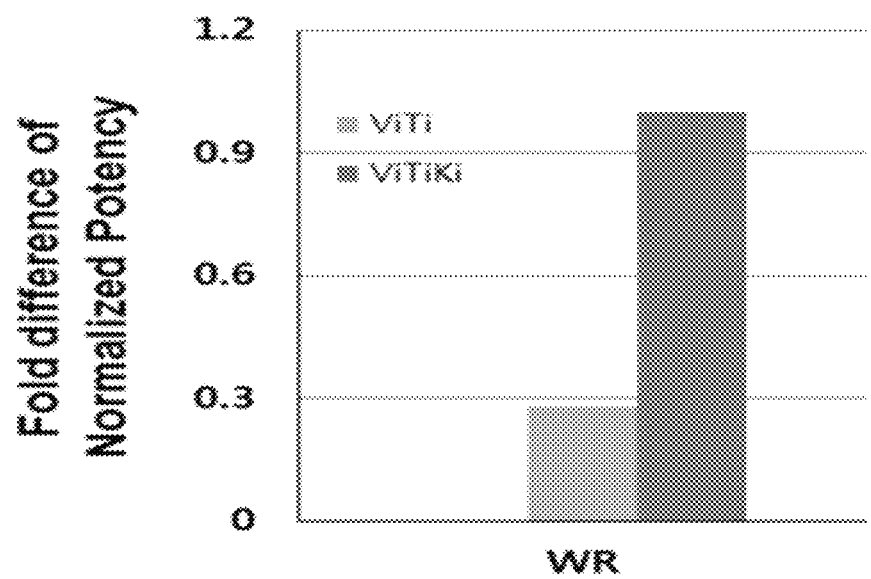

[Fig. 7A]
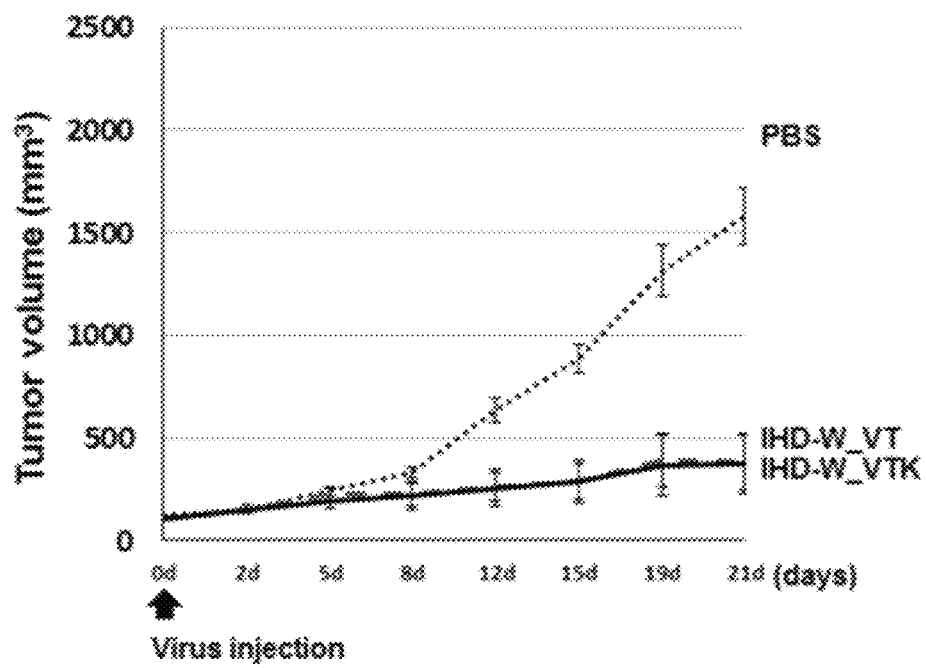
[Fig. 7B]
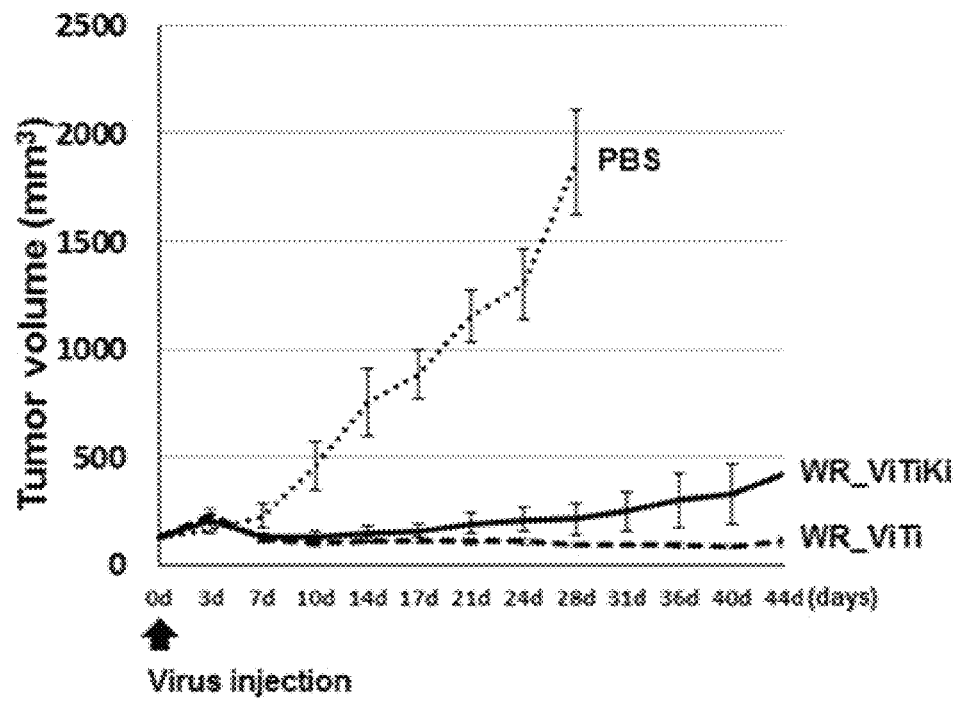

[Fig. 8A]
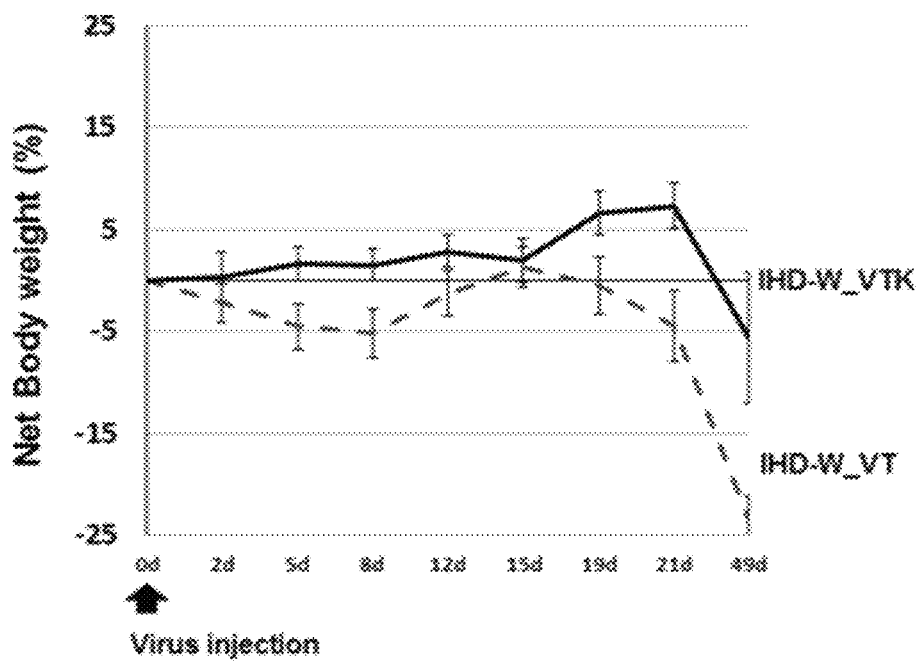
[Fig. 8B]
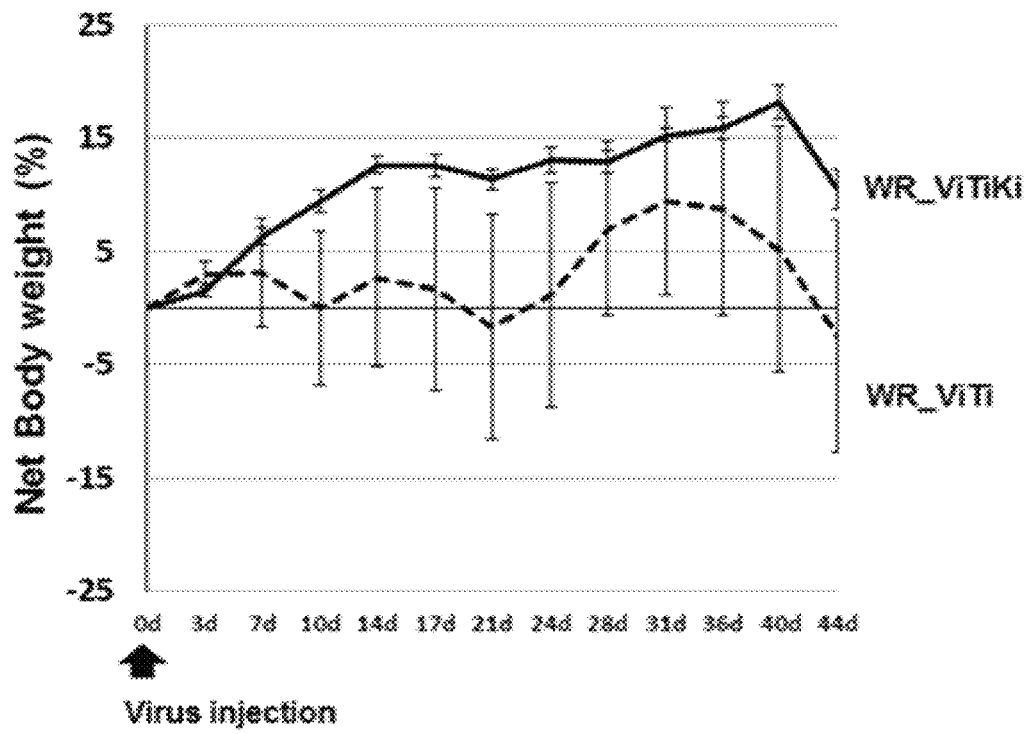

[Fig. 9A]
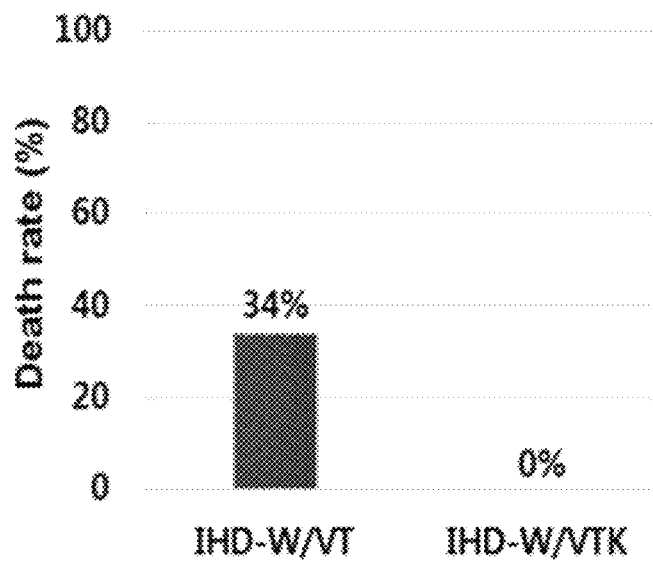
[Fig. 9B]
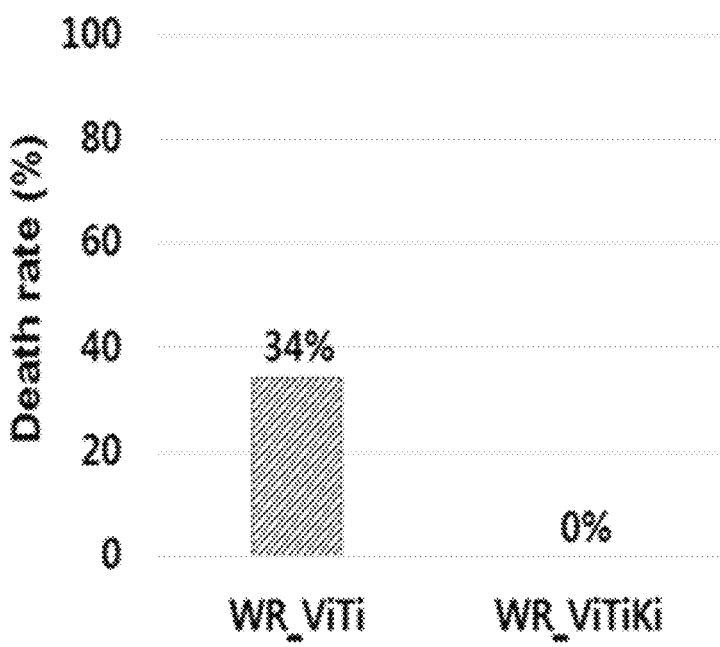

[Fig. 10A]
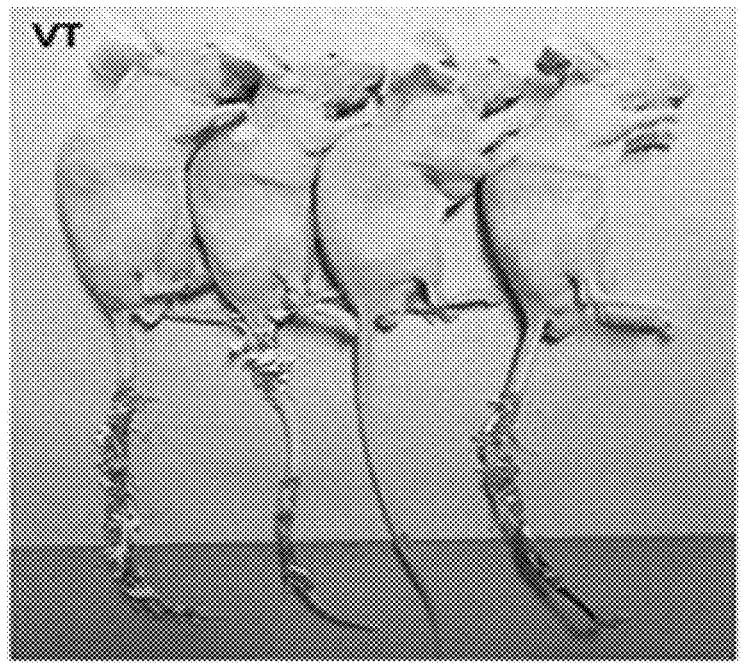
[Fig. 10B]
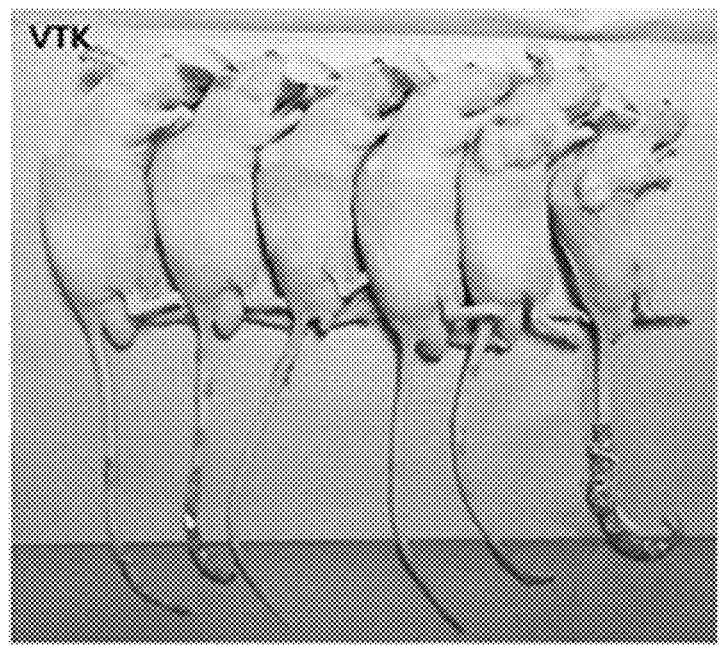

RECOMBINANT VACCINIA VIRUS AND USE THEREOF

CROSS REFERENCE TO RELATED APPLICATIONS

This application is a National Stage of International Application No. PCT/KR2017/007896 filed Jul. 21, 2017, claiming priority based on Korean Patent Application No. 10-2016-0092684 filed Jul. 21, 2016.

TECHNICAL FIELD

The present invention relates to a recombinant vaccinia virus in which expression of some genes is suppressed, and uses thereof.

BACKGROUND ART

Recently, studies on oncolytic viruses modified by genetically manipulating various viruses have been actively conducted for the purpose of developing cancer therapeutic agent. However, limitations of the oncolytic viruses have yet to be fully resolved. For example, in order to be developed into an anticancer agent, a virus having a tumor-selective replication ability was produced through genetic manipulation. However, there are limitations that the virus is replicated not only in cancer cells but also in normal cells, thereby killing the normal cells, or has insufficient anticancer effects. Accordingly, there is a continuing demand for the development of a technique which allows the oncolytic viruses to have increased selectivity and efficacy against cancer cells while minimizing influences on normal cells.

On the other hand, vaccinia virus is an enveloped DNA virus with double-stranded linear genomic DNA of about 200 kbp which encodes about 200 independent genes. The vaccinia virus was first used by Edward Jenner in the eighteenth century as a prophylactic vaccine for smallpox. Since then, the vaccinia virus has been developed into various prophylactic vaccines. In early vaccinia virus vaccines, a wild-type virus was used, and serious side effects such as systemic infection or progressive infection were seen in vaccinated patients. Therefore, in order to reduce side effects, modified vaccinia viruses with attenuated toxicity such as modified vaccinia Ankara (MVA), LC16m8 (derived from the Lister strain), and New York vaccinia virus (NYVAC, derived from the Copenhagen vaccinia strain) were developed. Vaccines that target various diseases have been developed based on these vaccinia viruses. Vaccinia virus strains such as Western Reserve (WR), NYVAC, Wyeth, and Lister are also being developed as oncolytic viruses.

Technical Problem

An object of the present invention is to provide a recombinant vaccinia virus in which the expression of some genes is suppressed, and an anticancer composition containing the recombinant vaccinia virus as an active ingredient.

Solution to Problem

In order to achieve the above object, the present invention provides a recombinant vaccinia virus in which expression of K3L, thymidine kinase (TK), and vaccinia growth factor (VGF) genes is suppressed.

In addition, the present invention provides a pharmaceutical composition for preventing or treating cancer which contains the recombinant vaccinia virus as an active ingredient.

Further, the present invention provides a method for preventing or treating cancer, comprising a step of administering the recombinant vaccinia virus to an individual.

Advantageous Effects of Invention

The recombinant vaccinia virus of the present invention selectively kills cancer cells and exhibits an excellent replication ability in cancer cells. In addition, due to having an excellent cancer cell-selective killing ability, the recombinant vaccinia virus has an advantage of being safer for use in the human body. Therefore, the recombinant vaccinia virus of the present invention can be usefully used as a composition for treating cancer.

BRIEF DESCRIPTION OF DRAWINGS

FIG. 1 is a schematic diagram showing a part of a construct of a shuttle plasmid which suppresses the expression of VGF gene of the present invention.

FIG. 2 is a schematic diagram showing a part of a construct of a shuttle plasmid which suppresses the expression of TK gene of the present invention.

FIG. 3 is a schematic diagram showing a part of a construct of a shuttle plasmid which suppresses the expression of K3L gene of the present invention.

FIG. 4A shows results which identify that various cancer cell lines as shown in Table 1-1 are killed by a recombinant virus in which expression of VGF, TK, and K3L genes is suppressed.

TABLE 1-1

| Carcinoma | Cell line |
| --- | --- |
| Lung cancer | A549 |
| Brain cancer | U-87MG |
| Breast cancer | T-47D |
| Ovarian cancer | A2780 |
| Pancreatic cancer | MIA PaCa-2 |
| Colorectal cancer | SW620 |

FIG. 4B shows results which identify that various cancer cell lines as shown in Table 1-2 are killed by the recombinant virus in which expression of VGF, TK, and K3L genes is suppressed.

TABLE 1-2

| Carcinoma | Cell line |
| --- | --- |
| Liver cancer | Hep3B |
| Prostate cancer | DU145 |
| Head and neck cancer | FaDu |
| Fibrosarcoma | HT-1080 |

FIG. 5 shows results which identify that a recombinant IHD-W vaccinia virus in which VGF, TK, and K3L genes are deleted or inactivated and expression of the genes is suppressed induces death of a colorectal cancer cell line. The meanings of abbreviations for the deleted genes are as shown in Table 2:

TABLE 2

| Abbreviation | Meaning |
| --- | --- |
| VTK | All of VGF, TK, and K3L genes are deleted |
| ViTK | Expression of VGF gene is inactivated, and both TK and K3L genes are deleted |
| VTiK | Expression of TK gene is inactivated, and both VGF and K3L genes are deleted |
| VTKi | Expression of K3L gene is inactivated, and both VGF and TK genes are deleted |

FIGS. 6A and 6B are graphs which identify a killing ability of a recombinant vaccinia virus, in which expression of K3L only or, both VGF and TK, or all VGF and TK and K3L genes being suppressed, against cancer cells relative to normal cells. FIG. 6A is a graph obtained by making a comparison for a killing ability of a recombinant IHD-W-K, IHD-W-VT or IHD-W-VTK vaccinia virus against cancer cells relative to normal cells, based on a IHD-W-VTK value; and FIG. 6B is a graph obtained by making a comparison for a killing ability of a recombinant WR-ViTi or WR-ViTiKi vaccinia virus against cancer cells relative to normal cells, based on a WR-ViTiKi value.

FIGS. 7A and 7B are graphs obtained by observing changes in tumor size after administration of a recombinant vaccinia virus, in which expression of both VGF and TK or all VGF and TK and K3L genes being suppressed, to a colorectal cancer mouse model. FIG. 7A is a graph obtained by observing changes in tumor size after administration of a recombinant IHD-W-VT or IHD-W-VTK vaccinia virus to a colorectal cancer mouse model; and FIG. 7B is a graph obtained by observing changes in tumor size after administration of a recombinant WR-ViTi or WR-ViTiKi vaccinia virus to a colorectal cancer mouse model.

FIGS. 8A and 8B are graphs which identify changes in body weight of mice on an individual basis after administration of a recombinant vaccinia virus, in which expression of both VGF and TK or all VGF and TK and K3L genes being suppressed, to a colorectal cancer mouse model. FIG. 8A is a graph which identifies changes in body weight of mice on an individual basis after administration of a recombinant IHD-W-VT or IHD-W-VTK vaccinia virus to a colorectal cancer mouse model; and FIG. 8B is a graph which identifies changes in body weight of mice on an individual basis after administration of a recombinant WR-ViTi or WR-ViTiKi vaccinia virus to a colorectal cancer mouse model.

FIGS. 9A and 9B are graphs which identify a mortality rate of mice after administration of a recombinant vaccinia virus, in which expression of both VGF and TK or all VGF and TK and K3L genes being suppressed, to a colorectal cancer mouse model. FIG. 9A is a graph which identifies a mortality rate of mice after administration of a recombinant IHD-W-VT or IHD-W-VTK vaccinia virus to a colorectal cancer mouse model; and FIG. 9B is a graph which identifies a mortality rate of mice after administration of a recombinant WR-ViTi or WR-ViTiKi vaccinia virus to a colorectal cancer mouse model.

FIGS. 10A and 10B show results which identify inflammation reaction in tails of mice after administration of a recombinant IHD-W vaccinia virus, in which expression of both VGF and TK or all VGF and TK and K3L genes being suppressed, to a colorectal cancer mouse model. FIG. 10A shows results which identify inflammatory response in tails of mice to which a recombinant IHD-W-VT vaccinia virus was administered, and FIG. 10B shows results of confirming inflammatory reaction in tails of mice to which a recombinant IHD-W-VTK vaccinia virus was administered.

DETAILED DESCRIPTION OF INVENTION

Hereinafter, the present invention will be described in detail.

In an aspect of the present invention, there is provided a recombinant vaccinia virus in which expression of VGF, TK, and K3L genes is suppressed.

The term "VGF" as used herein means vaccinia growth factor. The vaccinia growth factor is an enzyme exhibiting a similar activity to epithelial growth factor. The vaccinia growth factor encoded by the VGF gene exhibits a growth factor activity in the case of being infected with the virus and can be synthesized at an initial stage of infection caused by the virus. The VGF may be a sequence of GenBank: AAO89288.1, ABD52455.1, or AIX98927.1, but is not limited thereto. Specifically, the VGF may be a base sequence encoding an amino acid sequence represented by SEQ ID NO: 67, and the VGF gene may be a base sequence represented by SEQ ID NO: 66. The VGF or a gene thereof may have a homology of about 70% or 75% or more, and preferably about 80%, 81%, 82%, 83%, 84%, 85%, 86%, 87%, 88%, or 89% or more, to the amino acid sequence of SEQ ID NO: 67 or the base sequence of SEQ ID NO: 66. In addition, the VGF or a gene thereof may have a homology of about 90%, 91%, 92%, 93%, or 94% or more, preferably about 95%, 96%, 97%, 98%, or 99% or more, and most preferably about 99% or more, to the amino acid sequence of SEQ ID NO: 67 or the base sequence of SEQ ID NO: 66.

The term "TK" as used herein means thymidine kinase. The thymidine kinase is an enzyme involved in the biosynthesis of nucleotides. The thymidine kinase encoded by the TK gene causes a phosphoric acid at a γ position of ATP to bind to thymidine so that nucleotides constituting a viral DNA can be produced. The TK may be a sequence of GenBank: AAO89373.1, ABD52560.1, or AIX99011.1, but is not limited thereto. Specifically, the TK may be a base sequence encoding an amino acid sequence represented by SEQ ID NO: 69, and the TK gene may be a base sequence represented by SEQ ID NO: 68. The TK or a gene thereof may have a homology of about 70% or 75% or more, and preferably about 80%, 81%, 82%, 83%, 84%, 85%, 86%, 87%, 88%, or 89% or more, to the amino acid sequence of SEQ ID NO: 69 or the base sequence of SEQ ID NO: 68. In addition, the TK or a gene thereof may have a homology of about 90%, 91%, 92%, 93%, or 94% or more, preferably about 95%, 96%, 97%, 98%, or 99% or more, and most preferably about 99% or more, to the amino acid sequence of SEQ ID NO: 69 or the base sequence of SEQ ID NO: 68.

The term "K3L" as used herein means K3L protein. The K3L protein encoded by the K3L gene is a protein having homology to translation initiation factor-2α (eIF-2α) and can suppress an action of protein kinase R (PKR) which is an interferon activator. The K3L may be a sequence of GenBank: AAO89313.1, ABD52483.1, or AGB75754.1, but is not limited thereto. Specifically, the K3L may have a base sequence encoding an amino acid sequence represented by SEQ ID NO: 71, and the K3L gene may be a base sequence represented by SEQ ID NO: 70. The K3L or a gene thereof may have a homology of about 70% or 75% or more, and preferably about 80%, 81%, 82%, 83%, 84%, 85%, 86%, 87%, 88%, or 89% or more, to the amino acid sequence of SEQ ID NO: 71 or the base sequence of SEQ ID NO: 70. In addition, the K3L or a gene thereof may have a homology of about 90%, 91%, 92%, 93%, or 94% or more, preferably about 95%, 96%, 97%, 98%, or 99% or more, and most preferably about 99% or more, to the amino acid sequence of SEQ ID NO: 71 or the base sequence of SEQ ID NO: 70.

Suppressed expression of a gene according to the present invention means that the gene is not expressed or only a part of the gene is expressed by partial or entire deletion of the gene or insertion of a foreign gene into the gene so that an activity of a protein encoded by the gene is not exhibited. A method for deleting the gene or inserting a foreign gene can be performed by a method well known in the art. For example, this can be performed by methods for inserting a foreign gene which is disclosed in Molecular Cloning, A Laboratory Manual, Second Edition, by J. Sambrook, E. F. Fritsch and T. Maniatis (2003), Cold Spring Harbor Laboratory Press, Virology Methods Manual, edited by Brian W J Mahy and Hillar O Kangro (1996) Academic Press and Expression of genes by Vaccinia virus vectors, and Current Protocols in Molecular Biology, published by John Wiley and Son (1998), Chapter 16. Specifically, in an embodiment of the present invention, a foreign gene was inserted using pGEM-T Easy (Promega, Cat No. A1360) or pGEM-T (Promega, Cat No. A3600) vector system.

The vaccinia virus may be selected from the group consisting of Western Reserve (WR), New York Vaccinia Virus (NYVAC), Wyeth (The New York City Board of Health; NYCBOH), LC16m8, Lister, Copenhagen, Tian Tan, USSR, TashKent, Evans, International Health Division-J (IHD-J), International Health Division-White (IHD-W), and variants thereof, but is not limited thereto. Specifically, the vaccinia virus may be WR, Lister, or IHD-W vaccinia virus, and may have a sequence of GenBank: AY243312.1, DQ121394.1, or AIX98951.1. In an embodiment of the present invention, the vaccinia virus may be IHD-W.

The term "V" or "virus V" as used herein means a recombinant vaccinia virus in which VGF which is a vaccinia growth factor gene is deleted, and the virus does not express VGF gene due to deletion of the VGF gene.

In addition, the term "Vi" or "virus Vi" as used herein means a recombinant vaccinia virus in which expression of vaccinia growth factor is inactivated, and the virus does not express VGF gene. Expression of the vaccinia growth factor can be suppressed by inserting a foreign gene into the VGF gene.

In addition, the term "T" or "virus T" as used herein means a recombinant vaccinia virus in which thymidine kinase (TK) gene is deleted, and the virus does not express the TK gene due to deletion of the TK gene.

In addition, the term "Ti" or "virus Ti" as used herein means a recombinant vaccinia virus in which expression of thymidine kinase is inactivated, and the virus does not express TK gene. Expression of the thymidine kinase can be suppressed by inserting a foreign gene into the TK gene.

In addition, the term "K" or "virus K" as used herein means a recombinant vaccinia virus in which K3L gene is deleted, and the virus does not express the K3L gene due to deletion of the K3L gene.

In addition, the term "Ki" or "virus Ki" as used herein means a recombinant vaccinia virus in which expression of K3L gene is inactivated, and the virus does not express K3L. Expression of the K3L protein can be suppressed by inserting a foreign gene into the K3L gene.

In addition, the term "VT" or "virus VT" as used herein means a recombinant vaccinia virus in which VGF and TK genes are deleted. In addition, the term "ViTi" or "virus ViTi" as used herein means a recombinant vaccinia virus in which expression of vaccinia growth factor and thymidine kinase are inactivated. Methods for inactivating expression of the vaccinia growth factor and thymidine kinase are as described above.

In addition, the term "VTK" or "virus VTK" as used herein means a recombinant vaccinia virus in which VGF, TK, and K3L genes are deleted. In addition, the term "ViTiKi" or "virus ViTiKi" as used herein means a recombinant vaccinia virus in which expression of vaccinia growth factor, thymidine kinase, and K3L protein are inactivated. Methods for inactivating expression of the vaccinia growth factor, thymidine kinase, and K3L protein are as described above.

In addition, the term "ViTK" or "virus ViTK" as used herein means a recombinant vaccinia virus in which expression of vaccinia growth factor is inactivated, and TK and K3L genes are deleted. In addition, the term "VTiK" or "virus VTiK" as used herein means a recombinant vaccinia virus in which expression of thymidine kinase is inactivated, and VGF and K3L genes are deleted. In addition, the term "VTKi" or "virus VTKi" as used herein means a recombinant vaccinia virus in which expression of K3L protein is inactivated, and VGF and TK genes are deleted.

In addition, an aspect of the present invention provides a pharmaceutical composition for preventing or treating cancer which contains the recombinant vaccinia virus as an active ingredient.

Here, the recombinant vaccinia virus may be one in which expression of VGF, TK, and K3L genes are suppressed, as described above. The VGF, TK, and K3L genes are as described above.

As an example of the recombinant vaccinia virus, the following can be mentioned. Variants of WR vaccinia virus may be WR-VTK, WR-ViTiKi, WR-ViTK, WR-VTiK, or WR-VTKi. In addition, variants of NYVAC vaccinia virus may be NYVAC-VTK, NYVAC-ViTiKi, NYVAC-ViTK, NYVAC-VTiK, or NYVAC-VTKi. Furthermore, variants of Wyeth vaccinia virus may be Wyeth-VTK, Wyeth-ViTiKi, Wyeth-ViTK, Wyeth-VTiK, or Wyeth-VTKi. In addition, variants of LC16m8 vaccinia virus may be LC16m8-VTK, LC16m8-ViTiKi, LC16m8-ViTK, LC16m8-VTiK, or LC16m8-VTKi. Furthermore, variants of Lister vaccinia virus may be Lister-VTK, Lister-ViTiKi, Lister-ViTK, Lister-VTiK, or Lister-VTKi. In addition, variants of Copenhagen vaccinia virus may be Copenhagen-VTK, Copenhagen-ViTiKi, Copenhagen-ViTK, Copenhagen-VTiK, or Copenhagen-VTKi. Furthermore, variants of TianTan vaccinia virus may be TianTan-VTK, TianTan-ViTiKi, TianTan-ViTK, TianTan-VTiK, or TianTan-VTKi. In addition, variants of USSR vaccinia virus may be USSR-VTK, USSR-ViTiKi, USSR-ViTK, USSR-VTiK, or USSR-VTKi. Furthermore, variants of TashKent vaccinia virus may be TashKent-VTK, TashKent-ViTiKi, TashKent-ViTK, TashKent-VTiK, or TashKent-VTKi. In addition, variants of Evans vaccinia virus may be Evans-VTK, Evans-ViTiKi, Evans-ViTK, Evans-VTiK, or Evans-VTKi. Furthermore, variants of IHD-J vaccinia virus may be IHD-J-VTK, IHD-J-ViTiKi, IHD-J-ViTK, IHD-J-VTiK, or IHD-J-VTKi. Furthermore, variants of IHD-W vaccinia virus may be IHD-W-VTK, IHD-W-ViTiKi, IHD-W-VTiK, or IHD-W-VTKi.

According to an embodiment, it was identified that the recombinant vaccinia virus in which VGF, TK, and K3L genes are deleted has a killing ability against various cancer cells (FIGS. 4A and 4B). In addition, comparison on a cancer cell-killing ability was made by treating a colorectal cancer cell line with recombinant IHD-W-VTK, IHD-W-ViTK, IHD-W-VTiK, and IHD-W-VTKi vaccinia viruses. As a result, it was identified that all of the vaccinia viruses exhibited an excellent killing ability. Therefore, it was identified that regardless of whether a gene is deleted or inactivated, all of the vaccinia viruses in which expression of VTK gene is suppressed have an anticancer activity (FIG. 5). In addition, in a case where normal cells and cancer cells are treated with recombinant IHD-W-K, IHD-W-VT, IHD-W-VTK, WR-K, WR-ViTi, and WR-ViTiKi vaccinia viruses, it was identified that the recombinant IHD-W-VTK or WR-ViTiKi vaccinia virus in which expression of VGF, TK, and K3L genes is simultaneously suppressed exhibits a relatively superior killing ability against cancer cells relative to normal cells as compared to the recombinant IHD-W-K or WR-K vaccinia virus in which the only expression of K3L gene is suppressed or the recombinant IHD-W-VT or WR-ViTi vaccinia virus in which expression of VGF and TK genes are simultaneously suppressed (FIGS. 6A and 6B).

In addition, the recombinant IHD-W-VT and IHD-W-VTK vaccinia viruses and the recombinant WR-ViTi and WR-ViTiKi vaccinia viruses were administered to a tumor mouse model. As a result, it was identified that all of the viruses suppressed cancer growth (FIGS. 7A and 7B).

In addition, it was identified that a tumor mouse model to which the recombinant IHD-W-VTK or WR-ViTiKi vaccinia virus was administered exhibited lower weight loss and mortality rate than a tumor mouse model to which the recombinant IHD-W-VT or WR-ViTi vaccinia virus was administered (FIGS. 8A, 8B, 9A, and 9B). In addition, it was identified that mice to which the recombinant IHD-W-VTK vaccinia virus was administered exhibited a less inflammatory response in a tail region than mice to which the recombinant IHD-W-VT vaccinia virus was administered.

Accordingly, a pharmaceutical composition of the present invention for preventing or treating cancer which contains, as an active ingredient, a recombinant vaccinia virus in which expression of K3L, TK, and VGF genes is suppressed can be usefully used for preventing or treating cancer.

The term "cancer" as used herein may be solid cancer or blood cancer. Here, the solid tumor may be selected from the group consisting of lung cancer, colorectal cancer, prostate cancer, thyroid cancer, breast cancer, brain cancer, head and neck cancer, fibrosarcoma, esophageal cancer, skin cancer, thymic cancer, gastric cancer, colon cancer, liver cancer, ovarian cancer, uterine cancer, bladder cancer, rectal cancer, gallbladder cancer, biliary tract cancer, pancreatic cancer, and combinations thereof. According to an embodiment of the present invention, cancer may be lung cancer, liver cancer, prostate cancer, head and neck cancer, fibrosarcoma, brain cancer, breast cancer, ovarian cancer, pancreatic cancer, or colorectal cancer. In addition, the blood cancer may be selected from the group consisting of lymphoma, acute leukemia, multiple myeloma, and combinations thereof.

The pharmaceutical composition of the present invention may further contain one or more pharmaceutically acceptable additives selected from the group consisting of excipients, lubricants, wetting agents, sweeteners, fragrances, and preservatives.

The composition of the present invention may be formulated according to a conventional method. The composition of the present invention can be formulated employing a method known in the art so as to provide rapid, sustained, or delayed the release of an active ingredient, in particular after being administered to a mammal. According to the formulation, the composition of the present invention can be appropriately administered to an individual. Such administration may be parenteral administration, and examples thereof can include intra-cancer tissue, intradermal, intramuscular, intraperitoneal, intravenous, intraarterial, subcutaneous, intranasal, epidural, and oral route. A form of preparation for parenteral administration may be an injectable preparation.

In another aspect of the present invention, there is provided a method for preventing or treating cancer, comprising a step of administering the recombinant vaccinia virus to an individual.

The individual may be a mammal, in particular, a human. The composition of the present invention can be appropriately administered by a person skilled in the art depending on the patient's age, sex, weight, the severity of disease symptom, and route of administration. The administration may be once a day or several times a day.

A preferred dosage of the recombinant vaccinia virus of the present invention varies depending on condition and body weight of an individual, severity of disease, drug form, route of administration, and period, and can be appropriately selected by a person skilled in the art. Specifically, the dosage may be such that a patient receives virus particles, virus units having infectivity ($TCID_{50}$), or plaque forming units (pfu) of $1\times10^5$ to $1\times10^{18}$, and preferably $1\times10^5$, $2\times10^5$, $5\times10^5$, $1\times10^6$, $2\times10^6$, $5\times10^6$, $1\times10^7$, $2\times10^7$, $5\times10^7$, $1\times10^8$, $2\times10^8$, $5\times10^8$, $1\times10^9$, $2\times10^9$, $5\times10^9$, $1\times10^{10}$, $5\times10^{10}$, $1\times10^{11}$, $5\times10^{11}$, $1\times10^{12}$, $1\times10^{13}$, $1\times10^{14}$, $1\times10^{15}$, $1\times10^{16}$, $1\times10^{17}$ or more, in which various values and ranges therebetween can be included. In addition, a dosage of the virus may be 0.1 ml, 1 ml, 2 ml, 3 ml, 4 ml, 5 ml, 6 ml, 7 ml, 8 ml, 9 ml, 10 ml or more, and all values and ranges therebetween can be included.

Hereinafter, the present invention will be described in detail with reference to the following examples. However, the following examples are intended to illustrate the present invention, and the present invention is not limited thereto.

I. Production of Recombinant Vaccinia Virus

The present inventors constructed recombinant vaccinia virus vectors in which thymidine kinase (TK), vaccinia growth factor (VGF), and K3L genes are deleted or expression thereof is inactivated. Using these vectors, recombinant vaccinia viruses in which expression of the above genes is suppressed were produced and comparison was made for properties thereof as anti-cancer substances.

Example 1

Production of Recombinant WR Vaccinia Virus

Example 1.1

Construction of Recombinant WR Vaccinia Virus Vector in which VGF, TK, and K3L Genes are Inactivated or Deleted Example 1.1.1

Construction of Recombinant WR Vaccinia Virus Vector in which Expression of VGF Gene is Inactivated Genes that flank VGF gene on both sides in the genomic DNA of WR vaccinia virus (ATCC, Cat No. VR-1354) were amplified by PCR and inserted into pGEM-T Easy, respectively, to construct pGEM-T Easy-VGF-L(WR) and pGEM-T Easy-VGF-R(WR). Information on primers used for the amplification of homologous base sequences that flank the VGF gene on both sides is shown in Table 3.

TABLE 3

| Name | Sequence (5'→3') | SEQ ID NO |
|---|---|---|
| VGF-L forward (WR) | CGCAGCTGTGTTATCGATTGATAGTGGTGTCCT | SEQ ID NO: 1 |
| VGF-L reverse (WR) | CTGCAGCGCTAGCACCGCATAATCTGATAGCTGGAATA | SEQ ID NO: 2 |
| VGF-R forward (WR) | CGGGATCCGTTAATTAAACTCGACGAACTAAACTACCTATAC | SEQ ID NO: 3 |
| VGF-R reverse (WR) | CGATATCGGAAAATGTCTGTTAGTAAATAACCATC | SEQ ID NO: 4 |
| p11 promoter forward | CGGCTAGCTCTAGAAGCGATGCTACGCTAG | SEQ ID NO: 5 |
| p11 promoter reverse | CAAGCTTCGGTTGCCTCGAGGAATTCATTTATAGCATAGAA | SEQ ID NO: 6 |
| LacZ forward | CGCTCGAGGGATCCCGTCGTTTT | SEQ ID NO: 7 |
| LacZ reverse | ACAACGTCAAGCTTCTTAATTAAGGATCCCCCCTGCCCGGTTATTATTATTTTGACACCAGACCAACT | SEQ ID NO: 8 |

LacZ, whose expression is regulated by the p11 promoter, was used as a marker for screening for a virus in which recombination had occurred at a position of the VGF gene. A p11 promoter site in the WR gDNA was amplified by PCR and LacZ gene in pAAV-LacZ (Stratagene, Cat No. 240071-52) was amplified by PCR. Then, the resultants were inserted into pGEM-T Easy and pGEM-T, respectively, to construct pGEM-T Easy-p11 and pGEM-T-LacZ, respectively. Information on primers used for the amplification of the p11 promoter and the LacZ is shown in Table 3.

In order to construct a shuttle plasmid in which a function of the VGF gene is partially deleted, the pGEM-T Easy-VGF-L(WR) was treated with PvuII and PstI, and ligated with a vector obtained by treating pSP72 (Promega, Cat No. P2191) with PvuII and PstI, to construct pSP72-VGF-L(WR). In addition, the pGEM-T Easy-VGF-L-VGF-R(WR) was treated with EcoRV and BamHI, and ligated with a vector obtained by treating the pSP72-VGF-L(WR) as constructed above with EcoRV and BamHI, to secure pSP72-VGF-L-VGF-R(WR). In order to introduce a LacZ expression cassette, the PGEM-T Easy-p11 was treated with SalI and NheI, and ligated with a vector obtained by treating the pSP72-VGF-L-VGF-R(WR) with SalI and NheI, to construct pSP72-VGF-L-p11-VGF-R(WR). The constructed pSP72-VGF-L-p11-VGF-R(WR) was treated with EcoRI and PacI, and then the pGEM-T-LacZ as constructed above was cut with EcoRI and PacI. The resultants were ligated to complete pSP72-VGF-L-p11-LacZ-VGF-R(WR) (hereinafter referred to as "WR VGF(i) shuttle plasmid") which is a VGF shuttle plasmid.

Example 1.1.2

Construction of Recombinant WR Vaccinia Virus Vector in which Expression of TK Gene is Inactivated In order to secure genes that flank TK gene on both sides in the genomic DNA of WR vaccinia virus, the gDNA of WR was amplified by PCR, and then the base sequence segments which flank the TK gene on the left and right sides, and are homologous to each other were inserted into pGEM-T Easy, to construct pGEM-T Easy-TK-L(WR) and pGEM-T Easy-TK-R(WR). Information for primers used for the amplification of the base sequences which are homologous to both sides of the TK gene is shown in Table 4.

TABLE 4

| Name | Sequence (5'→3') | SEQ ID NO: |
|---|---|---|
| TK-L forward (WR) | AGGTCGACTTGCGATCAATAAATGGATCACAAC | SEQ ID NO: 9 |
| TK-L reverse (WR) | TTAGCTGCAGTATGCGGCCGCAACAATGTCTGGAAAGAACTGTCC | SEQ ID NO: 10 |
| TK-R forward (WR) | CGGAATTCTGTGAGCGTATGGCAA | SEQ ID NO: 11 |
| TK-R reverse (WR) | TCGGGATCCTCAGTCTCATGTTCTCACCGG | SEQ ID NO: 12 |
| p7.5 promoter forward | AGGAAGCTTTCCAAACCCACCCGCTTTTTAT | SEQ ID NO: 13 |
| p7.5 promoter reverse | GAATTCGCACTAGTTCCGATCGCCGTGCAATAAATTAGAATATACCC | SEQ ID NO: 14 |
| EGFP forward | CGCTCGAGATGGTGAGCAAGGGCGAGG | SEQ ID NO: 15 |
| EGFP reverse | TGAGATCTTTACTTGTACAGCTCGTCCATG | SEQ ID NO: 16 |
| Gpt forward | CGACTAGTACACAAGACAGGCTTGCGAG | SEQ ID NO: 17 |
| Gpt reverse | CGGAATTCGGCCCACTCATAAATCCAGTT | SEQ ID NO: 18 |
| pSE/L promoter forward | CGAGCTGCAGATAAAAATTAATTAATTACCCGGGTACCAGGCCTAGATCTGTCGACTCGAGCTTATTTATATTCCAAAAAAAAAAATAAAATTTCAATTTTTAAGCTTCGGGATCCGCA | SEQ ID NO: 19 |
| pSE/L promoter reverse | TTGCGGATCCCGAAGCTTAAAAATTGAAATTTTATTTTTTTTTTTGGAATATAAATAAGCTCGAGTCGACAGATCTAGGCCTGGTACCCGGGTAATTAATTAATTTTTATCTGCAGCTCG | SEQ ID NO: 20 |
| TF forward | ATCGGCGGCCGCTTTTTATCTGCGCGGTTAACCGCCTTTTTATCCATCAGGTGATCTGTTTTTATTGTGGAGCTGCAGCGAT | SEQ ID NO: 21 |
| TF reverse | ATCGCTGCAGCTCCACAATAAAAACAGATCACCTGATGGATAAAAAGGCGGTTAACCGCGCAGATAAAAAGCGGCCGCCGAT | SEQ ID NO: 22 |

EGFP, whose expression is regulated by pSE/L promoter, and Gpt whose expression is regulated by p7.5 promoter, were used as markers for screening for a virus in which recombination had occurred at a position of the TK gene. A p7.5 promoter site was amplified by PCR using the WR gDNA as a template, and EGFP gene in pEGFP-N3 (Clontech, Cat No. 6080-1) and Gpt gene in DH5α (Takara, Cat No. 9057) were also amplified by PCR. Then, the resultants were inserted into pGEM-T Easy, respectively, to construct pGEM-T Easy-p7.5, pGEM-T Easy-EGFP, and pGEM-T Easy-Gpt, respectively. In addition, pSE/L promoter and TF were constructed through primer annealing. Sequences of primers used in the experiments are shown in Table 4.

The pGEM-T Easy-p7.5 and the annealed pSE/L promoter were treated with BamHI and PstI, respectively, and ligated to construct pGEM-T Easy-pSE/L-p7.5. The constructed pGEM-T Easy-pSE/L-p7.5 and pGEM-T Easy-EGFP were respectively treated with BglII and XhoI, and then ligated, to construct pGEM-T Easy-pSE/L-p7.5.

In order to construct a shuttle plasmid in which a function of the TK gene is partially deleted, the pSP72 was treated with EcoRI and BamHI, and the pGEM-T Easy-TK-R(WR) was treated with EcoRI and BamHI. Then, the resultants were ligated to construct pSP72-TK-R(WR). The constructed pSP72-TK-R(WR) was treated with XhoI and PstI, and ligated with the pSEM-T Easy-TK-L obtained by being treated with SalI and PstI, to construct pSP72-TK-L-TK-R (WR). In order to introduce an EGFP expression cassette, the constructed pSP72-TK-L-TK-R(WR) and pGEM-T Easy-EGFP-pSE/L-p7.5 were respectively treated with EcoRI and PstI, and ligated to construct pSP72-TK-L-EGFP-pSE/L-p7.5-TK-R(WR).

In addition, the constructed pSP72-TK-L-EGFP-pSE/L-p7.5-TK-R(WR) and the annealed TF oligomer were respectively treated with PstI and NotI, and ligated to construct pSP72-TK-L-TF-EGFP-pSE/L-p7.5-TK-R(WR). In order to introduce a Gpt expression cassette, the constructed pSP72-TK-L-TF-EGFP-pSE/L-p7.5-TK-R(WR) and pGEM-T Easy-Gpt were respectively treated with EcoRI and SpeI, and ligated to finally construct pSP72-TK-L-TF-EGFP-pSE/L-p7.5-Gpt-TK-R(WR) (hereinafter referred to as "WR TK(i) shuttle plasmid") which is a TK shuttle plasmid.

Example 1.1.3

Construction of Recombinant WR Vaccinia Virus Vector in which K3L Gene is Deleted Genes that flank K3L gene on both sides in the genomic DNA of WR vaccinia virus were amplified by PCR. Here, information on primers used for the amplification of homologous base sequences that flank the K3L gene on both sides is shown in Table 5. The amplified genes were respectively inserted into pGEM-T, to construct pGEM-T-K3L-L (WR) and pGEM-T-K3L-R(WR).

TABLE 5

| Name | Sequence (5'→3') | SEQ ID NO: |
|---|---|---|
| K3L-L forward (WR) | TCGGTCGACCATATGTTT AAACGACGCATTATCTG | SEQ ID NO: 23 |
| K3L-L reverse (WR) | TCGAAGCTTTTTTTATAC CGAACATAAAAATAAGGT TAATTAT | SEQ ID NO: 24 |
| K3L-R forward (WR) | TCGGATATCCTTGTTAAC GGGCTCGTAAATTGGG | SEQ ID NO: 25 |
| K3L-R reverse (WR) | TCGGGATCCTGATAATAC ACATATTTATTTAGGAAG CG | SEQ ID NO: 26 |
| TF forward | ATCGGCGGCCGCTTTTTA TCTGCGCGGTTAACCGCC TTTTTATCCATCAGGTGA TCTGTTTTTATTGTGGAG CTGCAGCGAT | SEQ ID NO: 27 |
| TF reverse | ATCGCTGCAGCTCCACAA TAAAAACAGATCACCTGA | SEQ ID NO: 28 |

TABLE 5 -continued

| Name | Sequence (5'→3') | SEQ ID NO: |
|---|---|---|
| | TGGATAAAAAGGCGGTTA ACCGCGCAGATAAAAAGC GGCCGCCGAT | |
| p7.5 promoter forward | AGGAAGCTTTCCAAACCC ACCCGCTTTTTAT | SEQ ID NO: 29 |
| p7.5 promoter reverse | CGTGGATCCCCGTGCAAT AAATTAGAATATA | SEQ ID NO: 30 |

In order to construct a shuttle plasmid in which the K3L gene was deleted, the TF primer shown in Table 5 was annealed, treated with EcoRI and EcoRV, and ligated with a vector obtained by treating the pSP72 with EcoRI and EcoRV, to construct pSP72-TF. In addition, pDsRed2 (Clontech, Cat No. 632404) was treated with EcoRI and BamHI, and ligated with a vector obtained by treating the pSP72-TF with EcoRI and BamHI, to construct pSP72-DsRed-TF. The pGEM-T-K3L-R(WR) as constructed above was treated with EcoRV and BamHI, and ligated with a vector obtained by treating the pSP72-DsRed-TF with EcoRV and BamHI, to construct pSP72-DsRed-TF-K3L-R(WR). Next, the pGEM-T-K3L-L(WR) as constructed above was treated with XhoI and HindIII, and ligated with a vector obtained by treating the pSP72-DsRed-TF-K3L-R(WR) with XhoI and HindIII, to construct pSP72-K3L-L-DsRed-TF-K3L-R (WR). Finally, the p7.5 promoter was amplified by PCR using the WR gDNA as a template and then inserted into pGEM-T Easy, to construct pGEM-T Easy-p7.5. Information on primers used in the PCR amplification is shown in Table 5. The pGEM-T Easy-p7.5 was treated with HindIII and BamHI, and ligated with a vector obtained by treating the pSP72-K3L-L-DsRed-TF-K3L-R(WR) with HindIII and BamHI, to construct pSP72-K3L-L-p7.5-DsRed-TF-K3L-R (WR) (hereinafter referred to as "WR K3L shuttle plasmid").

Example 1.1.4

Construction of Recombinant WR Vaccinia Virus Vector in which Expression of K3L Gene is Inactivated A gene that flanks K3L gene on the left side and a part of the K3L gene in the genomic DNA of WR vaccinia virus were amplified by PCR. Here, the amplification was carried out with the start codon of the K3L gene being placed immediately after the K3L-L sequence, and primers used for the amplification of the homologous sequence on the left side of the K3L gene are shown in Table 6. Here, a K3L-L-K3Li(WR) fragment which was amplified and includes a part that excludes and follows the start codon of the K3L gene was obtained and then ligated with a pGEM-T Easy vector, to construct pGEM-T Easy-K3L-L-K3Li(WR).

TABLE 6

| Name | Sequence (5'→3') | SEQ ID NO |
|---|---|---|
| K3L-Li forward | TGTACGTATATTTAGATGTT TTCAGCT | SEQ ID NO: 31 |
| K3L-Li reverse | ATAAGCTTCTTGCATTTTGT TATTCGT | SEQ ID NO: 32 |

TABLE 6 -continued

| Name | Sequence (5'→3') | SEQ ID NO |
|---|---|---|
| K3L-Ri forward | CGCAGATAAAAACATATCCTTGTTAAC | SEQ ID NO: 33 |
| K3L-Ri reverse | GTTAACAAGGATATGTTTTTATCTGCG | SEQ ID NO: 34 |

The WR K3L shuttle plasmid and pGEM-T Easy-K3L-L-K3Li(WR) as constructed in Example 1.1.3 were treated with SnaBI and HindIII, and ligated to construct pSP72-K3L-L-K3Li-p7.5-DsRed-TF-K3L-R(WR). In order to introduce the start codon of K3L into the constructed pSP72-K3L-L-K3Li-p7.5-DsRed-TF-K3L-R(WR), a point mutation was performed using primers as shown in Table 6, so that pSP72-K3L-L-K3Li-p7.5-DsRed-TF-K3L$_{ATG}$-K3L-R (WR) (hereinafter referred to as "WR K3L(i) shuttle plasmid") was finally constructed.

Example 1.2

Production of Recombinant WR Vaccinia Virus in which VGF, TK, and K3L Genes are Deleted or Inactivated Example 1.2.1

Production of WR Vaccinia Virus in which K3L Gene is Deleted

In order to secure a recombinant virus, HeLa (ATCC, Cat No. CCL-2) cells were prepared in a 6-well plate at a condition of 3×10⁵ cells/well and in a state of MEM medium containing 2% fetal bovine serum. Then, the HeLa cells were transfected with 2 μg of the WR K3L shuttle plasmid as constructed in Example 1.1.3 using jetPRIME (Polyplus, Cat No. 114-07) and simultaneously treated with 0.05 MOI of WR wild-type vaccinia virus. After 4 hours of incubation, the medium was replaced with MEM medium containing 5% fetal bovine serum, and then the cells were further incubated for 48 hours. Finally, the infected cells were collected with 500 μl of the medium, and then the cells were lysed by repeating freezing and thawing three times. The cell lysate was called a crude virus. The produced crude virus was used and subjected to plaque isolation 6 times so that purely isolated recombinant WR vaccinia virus K was secured.

Example 1.2.2

Production of Recombinant WR Vaccinia Virus in which Expression of VGF and TK Genes is Inactivated First, recombinant WR vaccinia virus Vi in which expression of VGF gene is inactivated was obtained in the same conditions and methods as in Example 1.2.1, except that WR VGF(i) shuttle plasmid was used. Thereafter, recombinant WR vaccinia virus ViTi in which expression of VGF and TK genes is inactivated was obtained in the same methods as above, except that WR TK(i) shuttle plasmid and recombinant WR vaccinia virus Vi were used.

Example 1.2.3

Production of Recombinant WR Vaccinia Virus in which Expression of VGF, TK, and K3L Genes is Inactivated First, recombinant WR vaccine virus ViTiKi in which expression of VGF, TK, and K3L genes is inactivated was obtained in the same conditions and methods as in Example 1.2.1, except that WR K3L(i) shuttle plasmid and recombinant WR vaccinia virus ViTi were used.

Example 2

Production of Recombinant IHD-W Vaccinia Virus

Example 2.1

Construction of Recombinant IHD-W Vaccinia Virus Vector in which VGF, TK, and K3L Genes are Deleted Example 2.1.1

Construction of Recombinant IHD-W Vaccinia Virus Vector in which VGF Gene is Deleted Genes that flank VGF gene on both sides in the genomic DNA of IHD-W vaccinia virus (ATCC, Cat No. VR-1441) were amplified by PCR. Here, information on primers used for the amplification of homologous base sequences that flank the VGF gene on both sides is shown in Table 7. In such a manner, VGF-L(IHD-W) and VGF-R(IHD-W) fragments were obtained and then ligated with a pGEM-T Easy vector to construct pGEM-T Easy-VGF-L(IHD-W) or pGEM-T Easy-VGF-R(IHD-W).

TABLE 7

| Name | Sequence (5'→3') | SEQ ID NO |
|---|---|---|
| VGF-L forward (IHD-W) | CGAAAGCTTGTAAGATGTTTAGAAAATGGATATTTC | SEQ ID NO: 35 |
| VGF-L reverse (IHD-W) | CTGGGATCCTAGGCTAGCGTGTAAATAATATAAAAATAACAATACAATATTG | SEQ ID NO: 36 |
| VGF-R forward (IHD-W) | CTGGAATTCGATTTAATTAATTTTTATAAATTTTTTTATGAGTATTTTTACAAAAAA | SEQ ID NO: 37 |
| VGF-R reverse (IHD-W) | TAGGGATCCCATCGATAGTACAATAACTTTTATGAAAT | SEQ ID NO: 38 |

The above pGEM-T Easy-VGF-R(IHD-W) was treated with EcoRI and BamHI, and Psp72 was treated with EcoRI and BglII. Then, the resultants were ligated to construct pSP72-VGF-R(IHD-W). The constructed pSP72-VGF-R (IHD-W) and pGEM-T Easy-VGF-L(IHD-W) were respectively treated with HindIII and BamHI, and ligated to construct pSP72-VGF-L-VGF-R(IHD-W).

Next, in order to introduce the p11 promoter and the LacZ gene into the pSP72-VGF-L-VGF-R(IHD-W), the p11-LacZ expression cassette in the WR VGF shuttle plasmid of Example 1.1.1 and the pSP72-VGF-L-VGF-R(IHD-W) were treated with NheI and PacI, and ligated to construct pSP72-VGF-L-p11-LacZ-VGF-R(IHD-W) (hereinafter referred to as "IHD-W VGF shuttle plasmid".

Example 2.1.2

Construction of Recombinant IHD-W Vaccinia Virus Vector in which TK Gene is Deleted In order to secure genes that flank TK gene on both sides in the genomic DNA of IHD-W vaccinia virus, PCR was performed, and as a result, TK-L(IHD-W) and TK-R(IHD-W) fragments were obtained. Here, primers used are shown in Table 8. The secured TK-R(IHD-W) fragment and the pSP72 vector were respectively treated with EcoRI and BglII, and ligated to construct pSP72-TK-R(IHD-W). In addition, the pSP72-TK-R(IHD-W) and the TK-L(IHD-W) fragment were respectively treated with PstI and BamHI, and ligated to construct pSP72-TK-L-TK-R(IHD-W).

The constructed pSP72-TK-L-TK-R(IHD-W) vector and the WR TK shuttle plasmid as constructed in Example 1.1.2 were respectively treated with EcoRI and NotI, and ligated to finally construct pSP72-TK-L-TF-EGFP-pSE/L-p7.5-Gpt-TK-R(IHD-W) (hereinafter referred to as “IHD-W TK shuttle plasmid”).

TABLE 8

| Name | Sequence (5'→3') | SEQ ID NO |
|---|---|---|
| TK-L forward (IHD-W) | GATCTGCAGCCCTCTTCAAGAACCCATTAG | SEQ ID NO: 39 |
| TK-L reverse (IHD-W) | TAGGGATCCTAGGCGGCCGCATGACAATAAAGAATTAATTATTGTTCACTT | SEQ ID NO: 40 |
| TK-R forward (IHD-W) | CATGAATTCTATTATATTTTTTATCTAAAAAACTAAAAATAAACAT | SEQ ID NO: 41 |
| TK-R reverse (IHD-W) | AGATCTATCGCTTTAGTAGTAGGAAATGTTTTATTG | SEQ ID NO: 42 |

Example 2.1.3

Construction of Recombinant IHD-W Vaccinia Virus Vector in which K3L Gene is Deleted Genes that flank K3L gene on both sides in the genomic DNA of IHD-W vaccinia virus were amplified by PCR and respectively inserted in pGEM-T Easy, to construct pGEM-T Easy-K3L-L(IHD-W) and pGEM-T Easy-K3L-R(IHD-W). Here, primers used are shown in Table 9.

In order to construct a gene expression cassette inside the K3L shuttle plasmid, p'7.5-DsRed gene cassette was amplified by PCR using the WR K3L shuttle plasmid as constructed in Example 1.1.3 as a template, and then inserted into pGEM-T Easy to construct pGEM-T Easy-p7.5-DsRed. Sequences of primers used for the amplification of the p7.5 promoter and the DsRed gene are shown in Table 9.

TABLE 9

| Name | Sequence (5'→3') | SEQ ID NO |
|---|---|---|
| K3L-L forward (IHD-W) | TCGGTCGACCATATGTTTAAACGACGCATTATCTG | SEQ ID NO: 43 |
| K3L-L reverse (IHD-W) | TCGAAGCTTTTTTTATACCGAACATAAAAATAAGGTTAATTAT | SEQ ID NO: 44 |
| K3L-R forward (IHD-W) | CGCAGATAAAAATCACTTGTTAACGGGCTCGTAA | SEQ ID NO: 45 |
| K3L-R reverse (IHD-W) | AAGCGCTAACATGGATTAGGAAGCGCTAACATGG | SEQ ID NO: 46 |
| p7.5-DsRed forward | AGGAAGCTTTCCAAACCCACCCGCTTTTTAT | SEQ ID NO: 47 |
| p7.5-DsRed reverse | CGGATATCTTTTTATCTGCGCGGTTAAC | SEQ ID NO: 48 |

The constructed pGEM-T Easy-p7.5-DsRed and pSP72 vectors were respectively treated with HindIII and EcoRV, and then ligated to complete pSP72-p7.5-DsRed. In addition, the constructed pSP72-p7.5-DsRed was treated with EcoRV and BglII, and the pGEM-T Easy-K3L-R(IHD-W) as constructed above was treated with EcoRV and BamHI. Then, the resultants were ligated to construct pSP72-p7.5-DsRed-K3L-R(IHD-W). The constructed pSP72-p7.5-DsRed-K3L-R(IHD-W) was treated with XhoI and HindIII, and the pGEM-T Easy-K3L-L(IHD-W) was treated with SalI and HindIII. Then, the resultants were ligated to finally construct pSP72-K3L-L-p7.5-DsRed-K3L-R(IHD-W) (hereinafter referred to as “IHD-W K3L shuttle plasmid”).

Example 2.1.4

Construction of Recombinant IHD-W Vaccinia Virus Vector in which Expression of VGF Gene was Inactivated Genes that flank VGF gene on both sides and the VGF gene in the genomic DNA of IHD-W vaccinia virus were amplified by PCR. Here, the amplification was carried out with the start codon of the VGF gene being placed immediately after the VGF-L sequence, and the other sequences of the VGF gene being placed before the VGF-R sequence. Information on primers used for the amplification of the homologous sequences that flank the VGF gene on both sides is shown in Table 10. In such a manner, VGF-L-$VGF_{ATG}$(IHD-W) and VGFi-VGF-R(IHD-W) fragments were obtained, and then InFusion cloning thereof into the IHD-W VGF shuttle plasmid was performed.

TABLE 10

| Name | Sequence (5'→3') | SEQ ID NO |
|---|---|---|
| VGF-L-$VGF_{ATG}$ forward (IHD-W) | CGAGCAGCTGAAGCTTGTAAGATGTTTAGAAAATGGATATTTCC | SEQ ID NO: 49 |
| VGF-L-$VGF_{ATG}$ reverse (IHD-W) | CGCTTCTAGAGCTAGCCATTTTTGATGGATTTTGTGTTTATGCT | SEQ ID NO: 50 |
| VGF-Ri forward (IHD-W) | CAGGGGGGATCCTTAATTAATCGATGAAATATCTGATGTTGTTGTT | SEQ ID NO: 51 |
| VGF-Ri reverse (IHD-W) | TATAGTCAATAGATCTGGAAAATGTCTGTTAGTAAATAACCA | SEQ ID NO: 52 |
| $VGF_{ATGTAA}$ forward (IHD-W) | CATCGCTTCTAGAGCTAGCTTACATTTTTGATGGATTTTGTGTTTA | SEQ ID NO: 53 |

The IHD-W VGF shuttle plasmid was treated with NheI and HindIII, and the amplified VGF-L-VGF$_{ATG}$(IHD-W) fragment was InFusion cloned thereinto, to construct pSP72-VGF-L-VGF$_{ATG}$-p11-LacZ-VGF-R (IHR-W). The constructed pSP72-VGF-L-VGF$_{ATG}$-p11-LacZ-VGF-R(IHD-W) was treated with PacI and BglII, and the amplified VGFi-VGF-R(IHD-W) fragment was InFusion cloned thereinto, to construct pSP72-VGF-L-VGF$_{ATG}$-p11-LacZ-VGFi-VGF-R(IHD-W).

Next, in order to introduce a stop codon after the start codon of VGF into the pSP72-VGF-L-VGF$_{ATG}$-p11-LacZ-VGF-Ri(IHD-W), a point mutation was performed using primers as shown in Table 10, to construct pSP72-VGF-L-VGF$_{ATGTAA}$-p11-LacZ-VGFi-VGF-R(IHD-W) (hereinafter referred to as "IHD-W VGF(i) shuttle plasmid").

Example 2.1.5

Construction of Recombinant IHD-W Vaccinia Virus Vector in which Expression of TK Gene is Inactivated In order to acquire genes that flank TK gene on both sides and the TK gene from the genomic DNA of IHD-W vaccinia virus and the IHD-W TK shuttle plasmid, PCR was performed, and primers used are shown in Table 11. Here, the amplification was carried out with the start codon of the TK gene being placed immediately after the TK-L sequence, and the other sequences of the TK gene being placed before the TK-R sequence. In such a manner, TK-L-TK$_{ATG}$-TF-EGFP-pSE/L-p7.5-Gpt(IHD-W) fragment was obtained from the IHD-W TK shuttle plasmid and TK-TK-R(IHD-W) fragment was obtained from the IHD-W vaccinia genomic DNA. Then, InFusion cloning of the resultants into the IHD-W TK shuttle plasmid was performed.

TABLE 11

| Name | Sequence (5'→3') | SEQ ID NO |
|---|---|---|
| TK-Li forward (IHD-W) | TATTGTCATGCGGCCGCATGGTCGA CAACGGCGGACATATTCAGTTGAT | SEQ ID NO: 54 |
| TK-Li reverse (IHD-W) | ATCATGATGGCGGCCGTCAATTAGC ATCCATTTGATGATC | SEQ ID NO: 55 |
| TK-Ri forward (IHD-W) | ATTCTTTATTGTCATCATGGCGGCC GCTTTTTATCTGCGCGGTTAACC | SEQ ID NO: 56 |
| TK-Ri reverse (IHD-W) | GTCCGCCGTTGTCGACGGCCCACTC ATAAATCCAGTT | SEQ ID NO: 57 |

The IHD-W TK shuttle plasmid was treated with EagI and the amplified TKi-TK-R(IHD-W) fragment was InFusion cloned thereinto, to construct pSP72-TK-L-TKi-TK-R(IHD-W). The constructed pSP72-TK-L-TKi-TK-R(IHD-W) was treated with NotI and SalI, and the amplified TK-L-TK$_{ATG}$-TF-EGFP-pSE/L-p7.5-Gpt(IHD-W) fragment was InFusion cloned thereinto, to construct pSP72-TK-L-TK$_{ATG}$-TF-EGFP-pSE/L-p7.5-Gpt-TKi-TK-R(IHD-W) (hereinafter referred to as "IHD-W TK(i) shuttle plasmid").

Example 2.1.6

Construction of Recombinant IHD-W Vaccinia Virus Vector in which Expression of K3L Gene is Inactivated A gene that flanks K3L gene on the left side and a part of the K3L gene in the genomic DNA of IHD-W vaccinia virus were acquired through PCR. Primers used are shown in Table 12. Here, a K3L-L-K3Li(IHD-W) fragment which was amplified and includes a part that excludes and follows the start codon of the K3L gene was obtained and then InFusion cloning thereof into the IHD-W K3L shuttle plasmid was performed.

TABLE 12

| Name | Sequence (5'→3') | SEQ ID NO |
|---|---|---|
| K3L-Li forward (IHD-W) | GTTAGATCAGTGTACGTA TATTTAGAT | SEQ ID NO: 58 |
| K3L-Li reverse (IHD-W) | TGGGTTTGGAAAGCTTCT TGCATTTTGTTATTCGT | SEQ ID NO: 59 |
| K3L-Ri forward (IHD-W) | CGCAGATAAAAACATATC CTTGTTAAC | SEQ ID NO: 60 |
| K3L-Ri reverse (IHD-W) | GTTAACAAGGATATGTTT TTATCTGCG | SEQ ID NO: 61 |

The IHD-W K3L shuttle plasmid was treated with SnaBI and HindIII, and the amplified K3Li-L-K3L(IHD-W) fragment was InFusion cloned thereinto, to construct pSP72-K3L-L-K3Li(IHD-W). In order to introduce the start codon of K3L into the constructed pSP72-K3L-L-K3Li-p7.5-DsRed-TF-K3L-R(IHD-W), a point mutation was performed using primers as shown in Table 12, so that pSP72-K3L-L-K3Li-p7.5-DsRed-TF-K3L$_{ATG}$-K3L-R(IHD-W) (hereinafter referred to as "IHD-W K3L(i) shuttle plasmid") was finally constructed.

Example 2.2

Construction of Recombinant IHD-W Vaccinia Virus in which VGF, TK, and K3L Genes are Deleted Example 2.2.1

Production of Recombinant IHD-W Vaccinia Virus in which K3L Gene is Deleted

Using the IHD-W K3L shuttle plasmid as constructed in Example 2.1.3., a vaccinia virus in which K3L gene is deleted was produced by the following method.

In order to secure a recombinant virus, HeLa cells were prepared in a 6-well plate at a condition of 3×10$^5$ cells/well and in a state of MEM medium containing 2% fetal bovine serum. Then, the HeLa cells were transfected with 2 μg of the IHD-W K3L shuttle plasmid using jetPRIME and simultaneously treated with 0.05 MOI of IHD-W wild-type vaccinia virus. After 4 hours of incubation, the medium was replaced with MEM medium containing 5% fetal bovine serum, and then the cells were further incubated for 48 hours. Finally, the infected cells were collected with 500 μl of the medium, and then the cells were lysed by repeating freezing and thawing three times. The cell lysate was repeatedly subjected to freezing and thawing three times, to obtain the crude virus. The crude virus was used and repeatedly subjected to plaque isolation by a conventional method so that purely isolated recombinant IHD-W vaccinia virus K was obtained.

Example 2.2.2

Production of Recombinant IHD-W Vaccinia Virus in which VGF and TK Genes are Deleted The VGF and TK shuttle plasmids as constructed in Examples 2.1.1. and 2.1.2, respectively, were used to produce a vaccinia virus in which VGF and TK genes are deleted.

First, recombinant IHD-W vaccinia virus V in which VGF gene is deleted was obtained in the same conditions and methods as in Example 2.2.1, except that the IHD-W VGF shuttle plasmid was used. Thereafter, recombinant IHD-W vaccinia virus VT in which VGF and TK genes are deleted was obtained in the same methods as above, except that the IHD-W TK shuttle plasmid and the recombinant IHD-W vaccinia virus V were used.

Example 2.2.3

Production of Recombinant IHD-W Vaccinia Virus in which VGF, TK, and K3L Genes are Deleted The K3L shuttle plasmid as constructed in Example 2.1.3. was used to produce a recombinant IHD-W vaccinia virus in which VGF, TK, and K3L genes are deleted.

Recombinant IHD-W vaccinia virus VTK in which VGF, TK, and K3L genes are deleted was obtained in the same conditions and methods as in Example 2.2.1, except that the IHD-W K3L shuttle plasmid and the recombinant IHD-W vaccinia virus VT were used.

Example 2.2.4

Production of Recombinant IHD-W Vaccinia Virus in which Expression of VGF Gene is Inactivated and TK and K3L Genes are Deleted The VGF(i), TK, and K3L shuttle plasmids as constructed in Examples 2.1.4, 2.1.2, and 2.1.3, respectively, were used to produce a recombinant IHD-W vaccinia virus in which expression of VGF gene is inactivated, and TK and K3L genes are deleted.

First, recombinant IHD-W vaccinia virus T in which TK gene is deleted was obtained in the same conditions and methods as in Example 2.2.1, except that the IHD-W TK shuttle plasmid was used. Then, recombinant IHD-W vaccinia virus TK in which TK and K3L genes are deleted was obtained in the same methods as above, except that the IHD-W K3L shuttle plasmid and the recombinant IHD-W vaccinia virus T were used.

In addition, recombinant IHD-W vaccinia virus ViTK in which expression of VGF gene is inactivated, and TK and K3L genes are deleted was obtained in the same methods as above, except that the IHD-W VGF(i) shuttle plasmid and the recombinant IHD-W vaccinia virus TK were used.

Example 2.2.5

Production of Recombinant IHD-W Vaccinia Virus in which Expression of TK Gene is Inactivated and VGF and K3L Genes are Deleted The TK(i), VGF, and K3L shuttle plasmids as constructed in Examples 2.1.5, 2.1.1, and 2.1.3, respectively were used to produce a recombinant IHD-W vaccinia virus in which expression of TK gene is inactivated and VGF and K3L genes are deleted.

First, recombinant IHD-W vaccinia virus V in which VGF gene is deleted was obtained in the same conditions and methods as in Example 2.2.1, except that the IHD-W VGF shuttle plasmid was used. Thereafter, recombinant IHD-W vaccinia virus VK in which VGF and K3L genes are deleted was obtained in the same methods as above, except that the IHD-W K3L shuttle plasmid and the recombinant IHD-W vaccinia virus V were used.

In addition, recombinant IHD-W vaccinia virus VTiK in which expression of TK gene is inactivated and VGF and K3L genes are deleted was obtained in the same methods as above, except that the IHD-W TK(i) shuttle plasmid and the recombinant IHD-W vaccinia virus VK were used.

Example 2.2.6

Production of Recombinant IHD-W Vaccinia Virus in which Expression of K3L Gene is Inactivated and VGF and TK Genes are Deleted The K3L(i), VGF, and TK shuttle plasmids as constructed in Examples 2.1.6, 2.1.1, and Example 2.1.2, respectively, were used to produce a recombinant IHD-W vaccinia virus in which expression of K3L gene is inactivated and VGF and TK genes are deleted.

First, recombinant IHD-W vaccinia virus V in which VGF gene is deleted was obtained in the same conditions and methods as in Example 2.2.1., except that the IHD-W VGF shuttle plasmid was used. Thereafter, recombinant IHD-W vaccinia virus VT in which the VGF and TK genes are deleted was obtained in the same methods as above, except that the IHD-W TK shuttle plasmid and the recombinant IHD-W vaccinia virus V were used.

In addition, recombinant IHD-W vaccinia virus VTKi in which expression of K3L gene is inactivated, and VGF and TK genes are deleted was obtained in the same methods as above, except that the IHD-W K3L(i) shuttle plasmid and the recombinant IHD-W vaccinia virus VT were used.

Example 3

Production of Recombinant Lister Vaccinia Virus

Example 3.1

Construction of Recombinant Lister Vaccinia Virus Vector in which VGF, TK, and K3L Genes are Deleted

Example 3.1.1

Construction of Recombinant Lister Vaccinia Virus Vector in which K3L Gene is Deleted Genes that flank K3L gene on both sides in the genomic DNA of Lister vaccinia virus (ATCC, VR-1549) were amplified by PCR. Here, information on primers used for the amplification of homologous base sequences that flank the K3L gene on both sides is shown in Table 13. In such a manner, K3L-L(Lister) and K3L-R(Lister) fragments were obtained and then InFusion cloning thereof was performed using the pSP72-p7.5-DsRed generated in the construction process of the IHD-W K3L shuttle plasmid.

TABLE 13

| Name | Sequence (5'→3') | SEQ ID NO |
|---|---|---|
| VGF-R forward (Lister) | CGCAGATAAAAAGATATCCTTGT TAACGGGCTCGTAAATTG | SEQ ID NO: 62 |
| VGF-R reverse (Lister) | GGAGACCGGCAGATCTTGATAAT ACACATATTTATTTAGGAAGCG | SEQ ID NO: 63 |
| VGF-L forward (Lister) | CACTATAGAACTCGAGCATATGT TTAAACGACGCATTATCTG | SEQ ID NO: 64 |
| VGF-L reverse (Lister) | TGGGTTTGGAAAGCTTTTTTTAT ACCGAACATAAAAATAAGG | SEQ ID NO: 65 |

The pSP72-p7.5-DsRed was treated with EcoRV and BglII, and the amplified K3L-R(Lister) fragment was InFusion cloned thereinto, to construct pSP72-p7.5-DsRed-K3L-R(Lister). The constructed pSP72-p7.5-DsRed-K3L-R(Lister) was treated with XhoI and HindIII, and the amplified K3L-L(Lister) fragment was InFusion cloned thereinto, to construct pSP72-K3L-L-p7.5-DsRed-K3L-R(Lister) (hereinafter referred to as Lister K3L shuttle plasmid) which is a K3L shuttle plasmid.

Example 3.2

Production of Recombinant Lister Vaccinia Virus in which VGF, TK, and K3L Genes are Deleted Example 3.2.1

Production of Recombinant Lister Vaccinia Virus in which VGF and TK Genes are Deleted In order to secure a recombinant virus, HeLa cells were prepared in a 6-well plate at a condition of $3\times10^5$ cells/well and in a state of MEM medium containing 2% fetal bovine serum. Then, the HeLa cells were transfected with 2 μg of the IHD VGF shuttle plasmid as constructed in Example 2.1.1. using jetPRIME and simultaneously treated with 0.05 MOI of Lister wild-type vaccinia virus. After 4 hours of incubation, the medium was replaced with MEM medium containing 5% fetal bovine serum, and then the cells were further incubated for 48 hours. Finally, the infected cells were collected with 500 μl of the medium, and then the cells were lysed by repeating freezing and thawing three times. The cell lysate was called crude virus. The produced crude virus was used and subjected to plaque isolation 6 times, so that purely isolated recombinant Lister vaccinia virus V was secured.

Recombinant Lister vaccinia virus VT in which the VGF and TK genes are deleted was secured in the same conditions and methods as described above, except that the recombinant Lister vaccinia virus V and the IHD-W TK shuttle plasmid as constructed in Example 2.1.2. were used.

Example 3.2.2

Production of Recombinant Lister Vaccinia Virus in which VGF, TK, and K3L Genes are Deleted In order to secure a recombinant virus, recombinant Lister vaccinia virus TK in which VGF, TK, and K3L genes are deleted was obtained in the same conditions and methods as in Example 3.2.1, except that the Lister K3L shuttle plasmid and the recombinant Lister vaccinia virus VT were used.

II. Identification of Tumor-Killing Ability of Recombinant Vaccinia Virus In Vitro Experimental Example 1

Identification of Cancer Cell-Killing Ability of Recombinant Vaccinia Virus in which VGF, TK, and K3L Genes are Deleted CCK-8 analysis was performed to identify whether the recombinant vaccinia virus VTK as produced in Example I. has a killing ability against various types of cancer cells.

In order to identify a cell-killing ability of the recombinant virus in various human cancer cell lines, cancer cell lines were prepared as shown in Table 14, incubated in an incubator under a condition of 37° C. and 5% $CO_2$, and then aliquoted into 96-well plates.

TABLE 14

| Carcinoma | Cell line | Medium used |
|---|---|---|
| Brain cancer | U-87MG (ATCC, HTB-14) | MEM medium containing 10% fetal bovine serum |
| Liver cancer | Hep3B (ATCC, HB-8064) | |
| Prostate cancer | DU145 (ATCC, HTB-81) | |
| Head and neck cancer | FaDu (ATCC, HTB-43) | |
| Fibrosarcoma | HT-1080 (KCLB, 10121) | |
| Breast cancer | T-47D (ATCC, HTB-133) | RPMI medium containing 10% fetal bovine serum and recombinant insulin |
| Pancreatic cancer | MIA PaCa-2 (KCLB, 21420) | DMEM medium containing 10% fetal bovine serum |
| Colorectal cancer | SW620 (KCLB, 60068) | RPMI medium containing 10% fetal bovine serum |
| Ovarian cancer | A2780 (Sigma-Aldrich, 93112519) | |
| Lung cancer | A549 (ATCC, Cat No. CCL-185) | |

Here, aliquoting was carried out such that the number of cells per well was $5\times10^4$ for SW620, $2\times10^4$ for A2780, A549, DU145, T-47D, and FaDu, $1\times10^4$ for Hep3B and HT-1080, and $5\times10^3$ for MIA PaCa-2 and U-87 MG. After 24 hours of the incubation, the cell lines were infected with the recombinant IHD-W vaccinia virus VTK, the recombinant WR vaccinia virus ViTiKi, or the recombinant Lister vaccinia virus VTK so that 0.5 MOI was achieved for each virus. Here, cells which had not been treated with a virus were used as a control group. After 3 to 5 days, the cells were stained with CCK-8 (Dojindo, Cat No. CK04) solution to identify survival rates of the cancer cell lines. The results are shown in FIGS. 4A and 4B.

As shown in FIGS. 4A and 4B, it was identified that in a case where the VGF, TK, and K3L genes are deleted or expression thereof is inactivated, a killing ability against various types of cancer cells was exhibited regardless of a strain of vaccinia.

Experimental Example 2

Identification of Cancer Cell-Killing Ability of Recombinant Vaccinia Virus in which VGF, TK, and K3L Genes are Deleted or Expression thereof is Inactivated In order to identify whether the genes of the present invention whose expression is suppressed in a recombinant vaccinia virus exhibit a different killing ability against cancer cells depending on methods of suppressing expression thereof, a degree of death of the colorectal cancer cell line SW620 caused by the recombinant IHD-W vaccinia viruses VTK, ViTK, VTiK, and VTKi as produced in Examples 1.2.9. to 1.2.12. was identified.

First, the human colorectal cancer cell line SW620 was incubated in an incubator under a condition of 37° C. and 5% $CO_2$ using RPMI medium containing 2% fetal bovine serum, and aliquoted into a 96-well plate. Here, the SW620 cells were aliquoted to be $5\times10^4$ per well. After 24 hours of the incubation, the cell line was respectively infected with recombinant IHD-W vaccinia viruses VTK, ViTK, VTiK, and VTKi so that 0.001, 0.01, 0.1, or 1 MOI was achieved. After 3 days, the cells were stained with the CCK-8 solution to identify $ED_{50}$. The results are shown in FIG. 5.

As can be seen from the results, both the virus in which the VTK genes are deleted and expression thereof is completely suppressed and the virus in which expression of the VTK genes is inactivated by structural destruction of the genes exhibited an excellent cancer cell-killing ability without a statistically significant difference.

Experimental Example 3

Identification of Cancer Cell-Selective Killing Ability of Recombinant Vaccinia Virus in which VGF, TK, and K3L Genes are Deleted Identification was made as to whether a recombinant vaccinia virus in which expression of the three genes of VGF, TK, and K3L required for proliferation of a vaccinia virus in cells is simultaneously suppressed has a selectively increased killing ability against cancer cells relative to normal cells as compared with a case of a recombinant vaccinia virus in which expression of the two genes of VGF and TK is simultaneously suppressed or a recombinant vaccinia virus in which expression of one gene of K3L is suppressed.

First, NHBE (Lonza, CC-2540) which is a normal human cell line and SW620 which is a human colorectal cancer cell line were incubated in an incubator under a condition of 37° C. and 5% $CO_2$ using BEBM Basal medium (Lonza, 3171) containing BEGM SingleQuot Kit Suppl. & Growth Factors (Lonza, CC-4175) for NHBE and RPMI medium containing 10% fetal bovine serum for SW620, and aliquoted into 96-well plates. Here, the NHBE and SW620 cells were respectively aliquoted so as to be $5\times10^3$ and $5\times10^4$ per well. After 24 hours of the incubation, the cell lines were respectively infected with recombinant vaccinia virus IHD-W K, VT, VTK, or WR K, ViTi, ViTiKi so that 0.001, 0.01, 0.1, or 1 MOI was achieved. After 3 days, the cells were stained with a CCK-8 solution to obtain $ED_{50}$ values. The $ED_{50}$ against the cancer cells was divided by the $ED_{50}$ of the normal cells, and then a comparison of a selective killing ability against cancer cells relative to normal cells was made based on a value corresponding to VTK(IHD-W) or ViTiKi (WR) in each virus group. The results are shown in FIGS. 6A and 6B.

As shown in FIGS. 6A and 6B, in a case of the recombinant IHD-W vaccinia virus, it can be identified that the IHD-W VT or VTK virus exhibits a superior killing ability against cancer cells relative to normal cells as compared to the IHD-W K virus in which expression of one gene of K3L is suppressed. In addition, it can be identified that the IHD-W VTK virus exhibits a superior cancer cell-selective killing ability relative to the IHD-W VT virus. In a case of the recombinant WR vaccinia virus, it can be identified that a killing ability of WR ViTiKi in which expression of the three genes is suppressed is superior as compared with WR ViTi. Here, $ED_{50}$ could not be obtained for WR K in which expression of one gene of K3L is suppressed due to a very low killing ability thereof against normal cells and cancer cells.

In conclusion, it can be identified that the recombinant vaccinia virus in which expression of the three genes of VGF, TK, and K3L is suppressed exhibits a superior cancer cell-selective killing ability as compared with the recombinant vaccinia virus in which expression of the K3L gene or the VGF and TK genes is suppressed.

III. Identification of Anti-Cancer Effects of Recombinant Vaccinia Virus In Vivo Experimental Example 4

Identification of Anti-Cancer Effects of Recombinant Vaccinia Virus in which Expression of VGF, TK, and K3L Genes is Suppressed in Tumor Animal Model Anti-tumor effects of the recombinant IHD-W vaccinia viruses VT and VTK, or the recombinant WR vaccinia viruses ViTi and ViTiKi, as produced in Example I, were identified in a mouse model.

First, SW620 cell line which is a colorectal cancer cell line was prepared by being incubated in RPMI medium containing 10% fetal bovine serum. In a case where cells that were being incubated in an incubator under a condition of 37° C. and 5% $CO_2$ occupy 70% to 80% of a dish, the cells were prepared for cancer cell inoculation. Prepared respective cancer cells were centrifuged at 1,500 rpm for 5 minutes at 4° C. to remove all supernatant, and the cells were prepared by adding an excipient (RPMI medium) thereto. $5\times10^6$ cells thus prepared were injected subcutaneously in the right flank of a nude mouse (nu/nu BALB/c mouse; Charles River Japan (Yokohama)) to prepare a colorectal cancer mouse model. After one week, in a case where a tumor grew to a size of approximately 70 to 100 $mm^3$, the prepared mouse models were divided into groups to be treated with PBS, IHD-W VT, IHD-W VTK, WR ViTi, and WR ViTiKi with 6 mice per group, and then viruses were administered once into the tumor at $5\times10^6$ $TCID_{50}$. The results of identifying a size of cancer cells after the administration of the viruses are shown in FIGS. 7A and 7B.

As shown in FIG. 7, the growth of cancer cells was suppressed in the recombinant IHD-W or WR vaccinia virus-treated group as compared with PBS (Welgene, Cat No. LB001-02)-treated group which is a control group. However, it was identified that there was no significant difference in anti-cancer effects between the recombinant IHD-W vaccinia virus and the WR vaccinia virus.

Experimental Example 5

Identification of Safety of Recombinant Vaccinia Virus in which Expression of VGF, TK, and K3L Genes is Suppressed In order to evaluate the safety of the recombinant vaccinia viruses VT (ViTi) and VTK (ViTiKi) of IHD-W and WR strains as produced in Example I, weight change, mortality rate, and inflammatory response of mice receiving the viruses were identified and are shown in FIGS. 8A to 10B.

As shown in FIGS. 8A and 8B, at days 49 after the administration of the recombinant IHD-W vaccinia viruses, the VT-administered group showed a weight loss rate of 25%, whereas the VTK-administered group showed a weight loss rate of about 5%. In addition, on days 44 after the administration of the recombinant WR vaccinia viruses, some individuals showed a weight loss rate of 45% in the ViTi-treated group, whereas no individual showed a weight loss rate in the ViTiKi-treated group. In addition, as shown in FIGS. 9A and 9B, following days 49 after the administration of the recombinant vaccinia viruses, for both IHD-W and WR strains, the VT (ViTi)-administered groups showed a mortality rate of 34%, whereas all individuals survived in the VTK (ViTiKi)-administered groups.

In addition, as shown in FIGS. 10A and 10B, it could be identified that mice which survived after the administration of VT of IHD-W strain showed a greater amount of inflammatory response in a tail region than mice receiving VTK of IHD-W strain.

From the above results, it can be seen that a case where expression of the three genes of VGF, TK, and K3L is suppressed in the recombinant vaccinia virus is remarkably superior in terms of safety in vivo as compared with a case where expression of the two genes of VGF and TK is suppressed in the recombinant vaccinia virus.

The invention claimed is:

1. A method for treating a cancer in a subject in need thereof, comprising administering to the subject an effective amount of a recombinant vaccinia virus in which K3L gene, thymidine kinase (TK) gene, and vaccinia growth factor (VGF) gene are deleted or inactivated, wherein the recombinant vaccinia virus has an increased cancer cell killing activity in comparison to a recombinant vaccinia virus in which TK gene alone is deleted or inactivated, and the recombinant vaccinia virus has an increased cancer cell killing activity in comparison to a recombinant vaccinia virus in which VGF gene and TK gene are deleted or inactivated.

2. The method of claim 1, wherein the cancer is any one selected from the group consisting of lung cancer, colorectal cancer, prostate cancer, breast cancer, brain cancer, head and neck cancer, esophageal cancer, skin cancer, liver cancer, ovarian cancer, pancreatic cancer, and a combination thereof.

3. The method of claim 1, wherein the VGF gene is a polynucleotide consisting of the sequence of SEQ ID NO: 66.

4. The method of claim 1, wherein the TK gene is a polynucleotide consisting of the sequence of SEQ ID NO: 68.

5. The method of claim 1, wherein the K3L gene is a polynucleotide consisting of the sequence of SEQ ID NO: 70.

6. The method of claim 1, wherein the vaccinia virus is any one selected from the group consisting of Western Reserve (WR), New York Vaccinia Virus (NYVAC), Wyeth (The New York City Board of Health), LC16m8, Lister, Copenhagen, Tian Tan, USSR, TashKent, Evans, International Health Division-J (IHD-J), International Health Division-White (IHD-W), and a variant thereof.

7. The method of claim 6, wherein the vaccinia virus is IHD-W.

8. The method of claim 1, wherein the cancer is solid cancer or blood cancer.

9. The method of claim 8, wherein the solid cancer is any one selected from the group consisting of lung cancer, colorectal cancer, prostate cancer, thyroid cancer, breast cancer, brain cancer, head and neck cancer, esophageal cancer, skin cancer, thymic cancer, gastric cancer, colon cancer, liver cancer, ovarian cancer, uterine cancer, bladder cancer, rectal cancer, gallbladder cancer, biliary tract cancer, pancreatic cancer, and a combination thereof.

10. The method of claim 8, wherein the blood cancer is any one selected from the group consisting of lymphoma, acute leukemia, multiple myeloma, and a combination thereof.

11. The method of claim 1, wherein the expressions of the K3L gene, TK gene, and VGF gene are deleted or inactivated by partial or entire deletion of the genes, and/or insertion of a foreign gene into the genes.

* * * * *

SEQUENCE LISTING

```
<160> NUMBER OF SEQ ID NOS: 71

<210> SEQ ID NO 1
<211> LENGTH: 33
<212> TYPE: DNA
<213> ORGANISM: Artificial Sequence
<220> FEATURE:
<223> OTHER INFORMATION: VGF-L forward primer (WR)

<400> SEQUENCE: 1
cgcagctgtg ttatcgattg atagtggtgt cct                          33

<210> SEQ ID NO 2
<211> LENGTH: 38
<212> TYPE: DNA
<213> ORGANISM: Artificial Sequence
<220> FEATURE:
<223> OTHER INFORMATION: VGF-L reverse primer (WR)

<400> SEQUENCE: 2
ctgcagcgct agcaccgcat aatctgatag ctggaata                     38

<210> SEQ ID NO 3
<211> LENGTH: 42
<212> TYPE: DNA
<213> ORGANISM: Artificial Sequence
<220> FEATURE:
<223> OTHER INFORMATION: VGF-R forward primer (WR)

<400> SEQUENCE: 3
cgggatccgt taattaaact cgacgaacta aactacctat ac                42

<210> SEQ ID NO 4
<211> LENGTH: 35
<212> TYPE: DNA
<213> ORGANISM: Artificial Sequence
<220> FEATURE:
<223> OTHER INFORMATION: VGF-R reverse primer (WR)

<400> SEQUENCE: 4
cgatatcgga aaatgtctgt tagtaaataa ccatc                        35

<210> SEQ ID NO 5
<211> LENGTH: 30
```

```
<212> TYPE: DNA
<213> ORGANISM: Artificial Sequence
<220> FEATURE:
<223> OTHER INFORMATION: p11 promoter forward primer (WR)

<400> SEQUENCE: 5
cggctagctc tagaagcgat gctacgctag                                        30

<210> SEQ ID NO 6
<211> LENGTH: 41
<212> TYPE: DNA
<213> ORGANISM: Artificial Sequence
<220> FEATURE:
<223> OTHER INFORMATION: p11 promoter reverse primer (WR)

<400> SEQUENCE: 6
caagcttcgg ttgcctcgag gaattcattt atagcataga a                           41

<210> SEQ ID NO 7
<211> LENGTH: 31
<212> TYPE: DNA
<213> ORGANISM: Artificial Sequence
<220> FEATURE:
<223> OTHER INFORMATION: LacZ forward primer (WR)

<400> SEQUENCE: 7
cgctcgaggg atcccgtcgt tttacaacgt c                                      31

<210> SEQ ID NO 8
<211> LENGTH: 61
<212> TYPE: DNA
<213> ORGANISM: Artificial Sequence
<220> FEATURE:
<223> OTHER INFORMATION: LacZ reverse primer (WR)

<400> SEQUENCE: 8
aagcttctta attaaggatc cccctgccc ggttattatt atttttgaca ccagaccaac        60
t                                                                       61

<210> SEQ ID NO 9
<211> LENGTH: 33
<212> TYPE: DNA
<213> ORGANISM: Artificial Sequence
<220> FEATURE:
<223> OTHER INFORMATION: TK-L forward primer (WR)

<400> SEQUENCE: 9
aggtcgactt gcgatcaata aatggatcac aac                                    33

<210> SEQ ID NO 10
<211> LENGTH: 45
<212> TYPE: DNA
<213> ORGANISM: Artificial Sequence
<220> FEATURE:
<223> OTHER INFORMATION: TK-L reverse primer (WR)

<400> SEQUENCE: 10
ttagctgcag tatgcggccg caacaatgtc tggaaagaac tgtcc                       45

<210> SEQ ID NO 11
<211> LENGTH: 24
<212> TYPE: DNA
<213> ORGANISM: Artificial Sequence
<220> FEATURE:
<223> OTHER INFORMATION: TK-R forward primer (WR)
```

<400> SEQUENCE: 11
cggaattctg tgagcgtatg gcaa                                              24

<210> SEQ ID NO 12
<211> LENGTH: 30
<212> TYPE: DNA
<213> ORGANISM: Artificial Sequence
<220> FEATURE:
<223> OTHER INFORMATION: TK-R reverse primer (WR)

<400> SEQUENCE: 12
tcgggatcct cagtctcatg ttctcaccgg                                        30

<210> SEQ ID NO 13
<211> LENGTH: 31
<212> TYPE: DNA
<213> ORGANISM: Artificial Sequence
<220> FEATURE:
<223> OTHER INFORMATION: p7.5 promoter forward primer (WR)

<400> SEQUENCE: 13
aggaagcttt ccaaacccac ccgctttta t                                       31

<210> SEQ ID NO 14
<211> LENGTH: 47
<212> TYPE: DNA
<213> ORGANISM: Artificial Sequence
<220> FEATURE:
<223> OTHER INFORMATION: p7.5 promoter reverse primer (WR)

<400> SEQUENCE: 14
gaattcgcac tagttccgat cgccgtgcaa taaattagaa tataccc                     47

<210> SEQ ID NO 15
<211> LENGTH: 27
<212> TYPE: DNA
<213> ORGANISM: Artificial Sequence
<220> FEATURE:
<223> OTHER INFORMATION: EGFP forward primer (WR)

<400> SEQUENCE: 15
cgctcgagat ggtgagcaag ggcgagg                                           27

<210> SEQ ID NO 16
<211> LENGTH: 30
<212> TYPE: DNA
<213> ORGANISM: Artificial Sequence
<220> FEATURE:
<223> OTHER INFORMATION: EGFP reverse primer (WR)

<400> SEQUENCE: 16
tgagatcttt acttgtacag ctcgtccatg                                        30

<210> SEQ ID NO 17
<211> LENGTH: 28
<212> TYPE: DNA
<213> ORGANISM: Artificial Sequence
<220> FEATURE:
<223> OTHER INFORMATION: Gpt forward primer (WR)

<400> SEQUENCE: 17
cgactagtac acaagacagg cttgcgag                                          28

<210> SEQ ID NO 18
<211> LENGTH: 29

```
<212> TYPE: DNA
<213> ORGANISM: Artificial Sequence
<220> FEATURE:
<223> OTHER INFORMATION: Gpt reverse primer (WR)

<400> SEQUENCE: 18
cggaattcgg cccactcata aatccagtt                                        29

<210> SEQ ID NO 19
<211> LENGTH: 121
<212> TYPE: DNA
<213> ORGANISM: Artificial Sequence
<220> FEATURE:
<223> OTHER INFORMATION: pSE/L promoter forward primer (WR)

<400> SEQUENCE: 19
cgagctgcag ataaaaatta attaattacc cgggtaccag gcctagatct gtcgactcga      60
gcttatttat attccaaaaa aaaaaaataa aatttcaatt tttaagcttc gggatccgca     120
a                                                                    121

<210> SEQ ID NO 20
<211> LENGTH: 121
<212> TYPE: DNA
<213> ORGANISM: Artificial Sequence
<220> FEATURE:
<223> OTHER INFORMATION: pSE/L promoter reverse primer (WR)

<400> SEQUENCE: 20
ttgcggatcc cgaagcttaa aaattgaaat tttatttttt tttttggaa tataaataag       60 ctcgagtcga cagatctagg cctggtaccc gggtaattaa ttaattttta tctgcagctc     120
g                                                                    121

<210> SEQ ID NO 21
<211> LENGTH: 82
<212> TYPE: DNA
<213> ORGANISM: Artificial Sequence
<220> FEATURE:
<223> OTHER INFORMATION: TF forward primer (WR)

<400> SEQUENCE: 21
atcggcggcc gcttttttatc tgcgcggtta accgcctttt tatccatcag gtgatctgtt     60
tttattgtgg agctgcagcg at                                               82

<210> SEQ ID NO 22
<211> LENGTH: 82
<212> TYPE: DNA
<213> ORGANISM: Artificial Sequence
<220> FEATURE:
<223> OTHER INFORMATION: TF reverse primer (WR)

<400> SEQUENCE: 22
atcgctgcag ctccacaata aaacagatc acctgatgga taaaaaggcg gttaaccgcg       60
cagataaaaa gcggccgccg at                                               82

<210> SEQ ID NO 23
<211> LENGTH: 35
<212> TYPE: DNA
<213> ORGANISM: Artificial Sequence
<220> FEATURE:
<223> OTHER INFORMATION: K3L-L forward primer (WR)

<400> SEQUENCE: 23
```
tcggtcgacc atatgtttaa acgacgcatt atctg					35

<210> SEQ ID NO 24
<211> LENGTH: 43
<212> TYPE: DNA
<213> ORGANISM: Artificial Sequence
<220> FEATURE:
<223> OTHER INFORMATION: K3L-L reverse primer (WR)

<400> SEQUENCE: 24
tcgaagcttt ttttataccg aacataaaaa taaggttaat tat					43

<210> SEQ ID NO 25
<211> LENGTH: 34
<212> TYPE: DNA
<213> ORGANISM: Artificial Sequence
<220> FEATURE:
<223> OTHER INFORMATION: K3L-R forward primer (WR)

<400> SEQUENCE: 25
tcggatatcc ttgttaacgg gctcgtaaat tggg					34

<210> SEQ ID NO 26
<211> LENGTH: 38
<212> TYPE: DNA
<213> ORGANISM: Artificial Sequence
<220> FEATURE:
<223> OTHER INFORMATION: K3L-R reverse primer (WR)

<400> SEQUENCE: 26
tcgggatcct gataatacac atatttattt aggaagcg					38

<210> SEQ ID NO 27
<211> LENGTH: 82
<212> TYPE: DNA
<213> ORGANISM: Artificial Sequence
<220> FEATURE:
<223> OTHER INFORMATION: TF forward primer (WR)

<400> SEQUENCE: 27
atcggcggcc gcttttttatc tgcgcggtta accgcctttt tatccatcag gtgatctgtt					60 tttattgtgg agctgcagcg at					82

<210> SEQ ID NO 28
<211> LENGTH: 82
<212> TYPE: DNA
<213> ORGANISM: Artificial Sequence
<220> FEATURE:
<223> OTHER INFORMATION: TF reverse primer (WR)

<400> SEQUENCE: 28
atcgctgcag ctccacaata aaaacagatc acctgatgga taaaaaggcg gttaaccgcg					60 cagataaaaa gcggccgccg at					82

<210> SEQ ID NO 29
<211> LENGTH: 31
<212> TYPE: DNA
<213> ORGANISM: Artificial Sequence
<220> FEATURE:
<223> OTHER INFORMATION: p7.5 promoter forward primer (WR)

<400> SEQUENCE: 29
aggaagcttt ccaaacccac ccgcttttta t					31

<210> SEQ ID NO 30
<211> LENGTH: 31
<212> TYPE: DNA
<213> ORGANISM: Artificial Sequence
<220> FEATURE:
<223> OTHER INFORMATION: p7.5 promoter reverse primer (WR)

<400> SEQUENCE: 30
cgtggatccc cgtgcaataa attagaatat a                            31

<210> SEQ ID NO 31
<211> LENGTH: 27
<212> TYPE: DNA
<213> ORGANISM: Artificial Sequence
<220> FEATURE:
<223> OTHER INFORMATION: K3L-Li forward primer (WR)

<400> SEQUENCE: 31
tgtacgtata tttagatgtt ttcagct                                 27

<210> SEQ ID NO 32
<211> LENGTH: 27
<212> TYPE: DNA
<213> ORGANISM: Artificial Sequence
<220> FEATURE:
<223> OTHER INFORMATION: K3L-Li reverse primer (WR)

<400> SEQUENCE: 32
ataagcttct tgcattttgt tattcgt                                 27

<210> SEQ ID NO 33
<211> LENGTH: 27
<212> TYPE: DNA
<213> ORGANISM: Artificial Sequence
<220> FEATURE:
<223> OTHER INFORMATION: K3L-Ri forward primer (WR)

<400> SEQUENCE: 33
cgcagataaa aacatatcct tgttaac                                 27

<210> SEQ ID NO 34
<211> LENGTH: 27
<212> TYPE: DNA
<213> ORGANISM: Artificial Sequence
<220> FEATURE:
<223> OTHER INFORMATION: K3L-Ri reverse primer (WR)

<400> SEQUENCE: 34
gttaacaagg atatgttttt atctgcg                                 27

<210> SEQ ID NO 35
<211> LENGTH: 36
<212> TYPE: DNA
<213> ORGANISM: Artificial Sequence
<220> FEATURE:
<223> OTHER INFORMATION: VGF-L forward primer(IHD-W)

<400> SEQUENCE: 35
cgaaagcttg taagatgttt agaaaatgga tatttc                       36

<210> SEQ ID NO 36
<211> LENGTH: 52
<212> TYPE: DNA
<213> ORGANISM: Artificial Sequence
<220> FEATURE:
<223> OTHER INFORMATION: VGF-L reverse primer(IHD-W)

<400> SEQUENCE: 36
ctgggatcct aggctagcgt gtaaataata taaaaataac aatacaatat tg    52

<210> SEQ ID NO 37
<211> LENGTH: 58
<212> TYPE: DNA
<213> ORGANISM: Artificial Sequence
<220> FEATURE:
<223> OTHER INFORMATION: VGF-R forward primer(IHD-W)

<400> SEQUENCE: 37
ctggaattcg atttaattaa tttttataaa tttttttttat gagtattttt acaaaaaa    58

<210> SEQ ID NO 38
<211> LENGTH: 38
<212> TYPE: DNA
<213> ORGANISM: Artificial Sequence
<220> FEATURE:
<223> OTHER INFORMATION: VGF-R reverse primer(IHD-W)

<400> SEQUENCE: 38
tagggatccc atcgatagta caataacttt tatgaaat    38

<210> SEQ ID NO 39
<211> LENGTH: 30
<212> TYPE: DNA
<213> ORGANISM: Artificial Sequence
<220> FEATURE:
<223> OTHER INFORMATION: TK-L forward primer (IHD-W)

<400> SEQUENCE: 39
gatctgcagc cctcttcaag aacccattag    30

<210> SEQ ID NO 40
<211> LENGTH: 51
<212> TYPE: DNA
<213> ORGANISM: Artificial Sequence
<220> FEATURE:
<223> OTHER INFORMATION: TK-L reverse primer (IHD-W)

<400> SEQUENCE: 40
tagggatcct aggcggccgc atgacaataa agaattaatt attgttcact t    51

<210> SEQ ID NO 41
<211> LENGTH: 46
<212> TYPE: DNA
<213> ORGANISM: Artificial Sequence
<220> FEATURE:
<223> OTHER INFORMATION: TK-R forward primer (IHD-W)

<400> SEQUENCE: 41
catgaattct attatatttt ttatctaaaa aactaaaaat aaacat    46

<210> SEQ ID NO 42
<211> LENGTH: 36
<212> TYPE: DNA
<213> ORGANISM: Artificial Sequence
<220> FEATURE:
<223> OTHER INFORMATION: TK-R reverse primer(IHD-W)

<400> SEQUENCE: 42
agatctatcg ctttagtagt aggaaatgtt ttattg    36

<210> SEQ ID NO 43
<211> LENGTH: 35

```
<212> TYPE: DNA
<213> ORGANISM: Artificial Sequence
<220> FEATURE:
<223> OTHER INFORMATION: K3L-L forward primer (IHD-W)

<400> SEQUENCE: 43
tcggtcgacc atatgtttaa acgacgcatt atctg                        35

<210> SEQ ID NO 44
<211> LENGTH: 43
<212> TYPE: DNA
<213> ORGANISM: Artificial Sequence
<220> FEATURE:
<223> OTHER INFORMATION: K3L-L reverse primer (IHD-W)

<400> SEQUENCE: 44
tcgaagcttt ttttataccg aacataaaaa taaggttaat tat               43

<210> SEQ ID NO 45
<211> LENGTH: 34
<212> TYPE: DNA
<213> ORGANISM: Artificial Sequence
<220> FEATURE:
<223> OTHER INFORMATION: K3L-R forward primer (IHD-W)

<400> SEQUENCE: 45
cgcagataaa aatcacttgt taacgggctc gtaa                         34

<210> SEQ ID NO 46
<211> LENGTH: 34
<212> TYPE: DNA
<213> ORGANISM: Artificial Sequence
<220> FEATURE:
<223> OTHER INFORMATION: K3L-R reverse primer (IHD-W)

<400> SEQUENCE: 46
aagcgctaac atggattagg aagcgctaac atgg                         34

<210> SEQ ID NO 47
<211> LENGTH: 31
<212> TYPE: DNA
<213> ORGANISM: Artificial Sequence
<220> FEATURE:
<223> OTHER INFORMATION: p7.5-DsRed  forward primer (IHD-W)

<400> SEQUENCE: 47
aggaagcttt ccaaacccac ccgcttttta t                            31

<210> SEQ ID NO 48
<211> LENGTH: 28
<212> TYPE: DNA
<213> ORGANISM: Artificial Sequence
<220> FEATURE:
<223> OTHER INFORMATION: p7.5-DsRed reverse primer (IHD-W)

<400> SEQUENCE: 48
cggatatctt tttatctgcg cggttaac                                28

<210> SEQ ID NO 49
<211> LENGTH: 44
<212> TYPE: DNA
<213> ORGANISM: Artificial Sequence
<220> FEATURE:
<223> OTHER INFORMATION: VGF-L-VGFatg  forward primer (IHD-W)

<400> SEQUENCE: 49
```
cgagcagctg aagcttgtaa gatgtttaga aaatggatat ttcc                           44

<210> SEQ ID NO 50
<211> LENGTH: 44
<212> TYPE: DNA
<213> ORGANISM: Artificial Sequence
<220> FEATURE:
<223> OTHER INFORMATION: VGF-L-VGFatg reverse primer (IHD-W)

<400> SEQUENCE: 50
cgcttctaga gctagccatt tttgatggat tttgtgttta tgct                           44

<210> SEQ ID NO 51
<211> LENGTH: 46
<212> TYPE: DNA
<213> ORGANISM: Artificial Sequence
<220> FEATURE:
<223> OTHER INFORMATION: VGF-Ri forward primer (IHD-W)

<400> SEQUENCE: 51
caggggggat ccttaattaa tcgatgaaat atctgatgtt gttgtt                         46

<210> SEQ ID NO 52
<211> LENGTH: 42
<212> TYPE: DNA
<213> ORGANISM: Artificial Sequence
<220> FEATURE:
<223> OTHER INFORMATION: VGF-Ri reverse primer (IHD-W)

<400> SEQUENCE: 52
tatagtcaat agatctggaa aatgtctgtt agtaaataac ca                             42

<210> SEQ ID NO 53
<211> LENGTH: 46
<212> TYPE: DNA
<213> ORGANISM: Artificial Sequence
<220> FEATURE:
<223> OTHER INFORMATION: VGFatgtaa forward primer (IHD-W)

<400> SEQUENCE: 53
catcgcttct agagctagct tacatttttg atggattttg tgttta                         46

<210> SEQ ID NO 54
<211> LENGTH: 49
<212> TYPE: DNA
<213> ORGANISM: Artificial Sequence
<220> FEATURE:
<223> OTHER INFORMATION: TK-Li forward primer (IHD-W)

<400> SEQUENCE: 54
tattgtcatg cggccgcatg gtcgacaacg gcggacatat tcagttgat                      49

<210> SEQ ID NO 55
<211> LENGTH: 40
<212> TYPE: DNA
<213> ORGANISM: Artificial Sequence
<220> FEATURE:
<223> OTHER INFORMATION: TK-Li reverse primer (IHD-W)

<400> SEQUENCE: 55
atcatgatgg cggccgtcaa ttagcatcca tttgatgatc                                40

<210> SEQ ID NO 56
<211> LENGTH: 48
<212> TYPE: DNA
<213> ORGANISM: Artificial Sequence

```
<220> FEATURE:
<223> OTHER INFORMATION: TK-Ri forward primer (IHD-W)

<400> SEQUENCE: 56
attctttatt gtcatcatgg cggccgcttt ttatctgcgc ggttaacc                    48

<210> SEQ ID NO 57
<211> LENGTH: 37
<212> TYPE: DNA
<213> ORGANISM: Artificial Sequence
<220> FEATURE:
<223> OTHER INFORMATION: TK-Ri reverse primer (IHD-W)

<400> SEQUENCE: 57
gtccgccgtt gtcgacggcc cactcataaa tccagtt                               37

<210> SEQ ID NO 58
<211> LENGTH: 27
<212> TYPE: DNA
<213> ORGANISM: Artificial Sequence
<220> FEATURE:
<223> OTHER INFORMATION: K3L-Li forward primer (IHD-W)

<400> SEQUENCE: 58
gttagatcag tgtacgtata tttagat                                          27

<210> SEQ ID NO 59
<211> LENGTH: 35
<212> TYPE: DNA
<213> ORGANISM: Artificial Sequence
<220> FEATURE:
<223> OTHER INFORMATION: K3L-Li reverse primer (IHD-W)

<400> SEQUENCE: 59
tgggtttgga aagcttcttg cattttgtta ttcgt                                 35

<210> SEQ ID NO 60
<211> LENGTH: 27
<212> TYPE: DNA
<213> ORGANISM: Artificial Sequence
<220> FEATURE:
<223> OTHER INFORMATION: K3L-Ri forward primer (IHD-W)

<400> SEQUENCE: 60
cgcagataaa aacatatcct tgttaac                                          27

<210> SEQ ID NO 61
<211> LENGTH: 27
<212> TYPE: DNA
<213> ORGANISM: Artificial Sequence
<220> FEATURE:
<223> OTHER INFORMATION: K3L-Ri reverse primer (IHD-W)

<400> SEQUENCE: 61
gttaacaagg atatgttttt atctgcg                                          27

<210> SEQ ID NO 62
<211> LENGTH: 41
<212> TYPE: DNA
<213> ORGANISM: Artificial Sequence
<220> FEATURE:
<223> OTHER INFORMATION: VGF-R forward primer (Lister)

<400> SEQUENCE: 62
cgcagataaa aagatatcct tgttaacggg ctcgtaaatt g                          41
```

<210> SEQ ID NO 63
<211> LENGTH: 45
<212> TYPE: DNA
<213> ORGANISM: Artificial Sequence
<220> FEATURE:
<223> OTHER INFORMATION: VGF-R reverse primer (Lister)

<400> SEQUENCE: 63
ggagaccggc agatcttgat aatacacata tttatttagg aagcg                45

<210> SEQ ID NO 64
<211> LENGTH: 42
<212> TYPE: DNA
<213> ORGANISM: Artificial Sequence
<220> FEATURE:
<223> OTHER INFORMATION: VGF-L forward primer (Lister)

<400> SEQUENCE: 64
cactatagaa ctcgagcata tgtttaaacg acgcattatc tg                   42

<210> SEQ ID NO 65
<211> LENGTH: 42
<212> TYPE: DNA
<213> ORGANISM: Artificial Sequence
<220> FEATURE:
<223> OTHER INFORMATION: VGF-L reverse primer (Lister)

<400> SEQUENCE: 65
tgggtttgga aagcttttttt tataccgaac ataaaaataa gg                  42

<210> SEQ ID NO 66
<211> LENGTH: 423
<212> TYPE: DNA
<213> ORGANISM: Vaccinia virus

<400> SEQUENCE: 66
atgtcgatga aatatctgat gttgttgttc gctgctatga taatcagatc attcgccgat    60
agtggtaacg ctatcgaaac gacattgcca gaaattacaa acgctacaac agatattcca   120
gctatcagat tatgcggtcc agagggagat ggatattgtt tacacggtga ctgtatccac   180
gctagagata tcgacggtat gtattgtaga tgctctcatg gttatacagg cattagatgt   240
cagcatgtag tattagtaga ctatcaacgt tcagaaaaac caaacactac aacgtcatat   300
atcccatctc ccggtattgt gcttgtatta gtaggcatta ttattatgtg ttgtctatta   360 tctgttttata ggttcactcg aagaactaat aaactacctc tacaagatat ggttgtgcca   420
taa                                                                 423

<210> SEQ ID NO 67
<211> LENGTH: 140
<212> TYPE: PRT
<213> ORGANISM: Vaccinia virus

<400> SEQUENCE: 67

Met Ser Met Lys Tyr Leu Met Leu Leu Phe Ala Ala Met Ile Ile Arg
1               5                   10                  15

Ser Phe Ala Asp Ser Gly Asn Ala Ile Glu Thr Thr Leu Pro Glu Ile
            20                  25                  30

Thr Asn Ala Thr Thr Asp Ile Pro Ala Ile Arg Leu Cys Gly Pro Glu
        35                  40                  45

Gly Asp Gly Tyr Cys Leu His Gly Asp Cys Ile His Ala Arg Asp Ile
    50                  55                  60

Asp Gly Met Tyr Cys Arg Cys Ser His Gly Tyr Thr Gly Ile Arg Cys
65                  70                  75                  80

Gln His Val Val Leu Val Asp Tyr Gln Arg Ser Glu Lys Pro Asn Thr
                85                  90                  95

Thr Thr Ser Tyr Ile Pro Ser Pro Gly Ile Val Leu Val Leu Val Gly
            100                 105                 110

Ile Ile Ile Met Cys Cys Leu Leu Ser Val Tyr Arg Phe Thr Arg Arg
        115                 120                 125

Thr Asn Lys Leu Pro Leu Gln Asp Met Val Val Pro
    130                 135                 140

<210> SEQ ID NO 68
<211> LENGTH: 534
<212> TYPE: DNA
<213> ORGANISM: Vaccinia virus

<400> SEQUENCE: 68
atgaacggcg gacatattca gttgataatc ggccccatgt tttcaggtaa aagtacagaa      60
ttaattagac gagttagacg ttatcaaata gctcaatata aatgcgtgac tataaaatat     120
tctaacgata atagatacgg aacgggacta tggacgcatg ataagaataa ttttgaagca     180
ttggaagcaa ctaaactatg tgatgtcttg gaatcaatta cagatttctc cgtgataggt     240
atcgatgaag acagttctt tccagacatt gttgaattct gtgagcgtat ggcaaacgaa      300
ggaaaaatag ttatagtagc cgcactcgat gggacatttc aacgtaaacc gtttaataat     360
attttgaatc ttattccatt atctgaaatg gtggtaaaac taactgctgt gtgtatgaaa     420
tgctttaagg aggcttcctt ttctaaacga ttgggtgagg aaaccgagat agaaataata     480
ggaggtaatg atatgtatca atcggtgtgt agaaagtgtt acatcgactc ataa           534

<210> SEQ ID NO 69
<211> LENGTH: 177
<212> TYPE: PRT
<213> ORGANISM: Vaccinia virus

<400> SEQUENCE: 69

Met Asn Gly Gly His Ile Gln Leu Ile Ile Gly Pro Met Phe Ser Gly
1               5                   10                  15

Lys Ser Thr Glu Leu Ile Arg Arg Val Arg Arg Tyr Gln Ile Ala Gln
            20                  25                  30

Tyr Lys Cys Val Thr Ile Lys Tyr Ser Asn Asp Asn Arg Tyr Gly Thr
        35                  40                  45

Gly Leu Trp Thr His Asp Lys Asn Asn Phe Glu Ala Leu Glu Ala Thr
    50                  55                  60

Lys Leu Cys Asp Val Leu Glu Ser Ile Thr Asp Phe Ser Val Ile Gly
65                  70                  75                  80

Ile Asp Glu Gly Gln Phe Phe Pro Asp Ile Val Glu Phe Cys Glu Arg
                85                  90                  95

Met Ala Asn Glu Gly Lys Ile Val Ile Val Ala Ala Leu Asp Gly Thr
            100                 105                 110

Phe Gln Arg Lys Pro Phe Asn Asn Ile Leu Asn Leu Ile Pro Leu Ser
        115                 120                 125

Glu Met Val Val Lys Leu Thr Ala Val Cys Met Lys Cys Phe Lys Glu
    130                 135                 140

Ala Ser Phe Ser Lys Arg Leu Gly Glu Glu Thr Glu Ile Glu Ile Ile
145                 150                 155                 160

```
<210> SEQ ID NO 70
<211> LENGTH: 267
<212> TYPE: DNA
<213> ORGANISM: Vaccinia virus

<400> SEQUENCE: 70
ttattgatgt ctacacatcc ttttgtaatt gacatctata tatccttttg tataatcaac    60
tctaatcact ttaactttta cagttttccc taccagttta tccctatatt caacatatct   120
atccatatgc atcttaacac tctctgccaa gatagcttca gagtgaggat agtcaaaaag   180
ataaatatat agagcataat ccttctcgta tactctgccc tttattacat cgcccgcatt   240
gggcaacgaa taacaaaatg caagcat                                       267

<210> SEQ ID NO 71
<211> LENGTH: 88
<212> TYPE: PRT
<213> ORGANISM: Vaccinia virus

<400> SEQUENCE: 71

Met Leu Ala Phe Cys Tyr Ser Leu Pro Asn Ala Gly Asp Val Ile Lys
1               5                   10                  15

Gly Arg Val Tyr Glu Lys Asp Tyr Ala Leu Tyr Ile Tyr Leu Phe Asp
            20                  25                  30

Tyr Pro His Ser Glu Ala Ile Leu Ala Glu Ser Val Lys Met His Met
        35                  40                  45

Asp Arg Tyr Val Glu Tyr Arg Asp Lys Leu Val Gly Lys Thr Val Lys
    50                  55                  60

Val Lys Val Ile Arg Val Asp Tyr Thr Lys Gly Tyr Ile Asp Val Asn
65                  70                  75                  80

Tyr Lys Arg Met Cys Arg His Gln
                85
```